US007118874B2

(12) United States Patent
Torres

(10) Patent No.: US 7,118,874 B2
(45) Date of Patent: Oct. 10, 2006

(54) IMMUNOGENIC FORMULATION AND PROCESS FOR PREPARATION THEREOF

(75) Inventor: José Vidal Torres, Davis, CA (US)

(73) Assignee: Variation Biotechnologies Inc., Ottawa (CA)

( * ) Notice: Subject to any disclaimer, the term of this patent is extended or adjusted under 35 U.S.C. 154(b) by 156 days.

(21) Appl. No.: 10/072,084

(22) Filed: Feb. 8, 2002

(65) Prior Publication Data

US 2002/0183484 A1 Dec. 5, 2002

Related U.S. Application Data

(63) Continuation-in-part of application No. 09/414,484, filed on Oct. 8, 1999, now abandoned.

(60) Provisional application No. 60/103,642, filed on Oct. 9, 1998.

(51) Int. Cl.
*G01N 33/53* (2006.01)
*C12P 21/02* (2006.01)

(52) U.S. Cl. .................. 435/7.1; 435/6; 435/5; 435/4; 435/DIG. 46; 424/189.1; 424/187.1; 424/193.1; 424/278.1; 530/350; 530/300; 514/2

(58) Field of Classification Search .......... 424/189.1, 424/187.1, 193.1, 278.1; 530/350, 300; 514/2; 435/7.1, 6, 4
See application file for complete search history.

(56) References Cited

U.S. PATENT DOCUMENTS

| 5,580,563 A | 12/1996 | Tam ................. 424/197.11 |
| 6,110,465 A | 8/2000 | Bukh et al. ............. 424/189.1 |

FOREIGN PATENT DOCUMENTS

WO    WO 94 00151    6/1994

OTHER PUBLICATIONS

Meyer, Debra, et al.; Hypervariable Epitope Constructs Representing Variability in Envelope Glycoprotein of SIV Induce a Broad Humoral Immune Response in Rabbits and Rhesus Macaques; AIDS Research and Human Retroviruses, 1998, 14.9, pp. 751-760.
Puntoriero, Giulia, et al.; Towards a Solution for Hepatitis C Virus Hypervaribility: Mimotopes of the Hypervariable Rgion 1 Can Induce Antibodies Cross-Reacting With a Large Number of Viral Variants; The EMBO Journal, 1998, 17.13, pp. 3521-3533.
Anderson, David E., et al.; Hypervariable Epitope Constructs As a Means of Accounting for Epitope Variability; Vaccine, 1994, 12.8, pp. 736-740.
Meyer, Debra and Torres, Jose V.; Hypervariable Epitope Construct: A Synthetic Immunogen That Overcomes MHC Restriction of Antigen Presentation; Molecular Immunology, 1999, 36, pp. 631-637.
Nardelli, B., et al.; A Chemically Defined Synthetic Vaccine Model for HIV-1;The Journal of Immunology, 1992, 148.3, pp. 914-920.
Prezzi, Caterina, et al.; Selection of Antigenic and Immunogenic Mimics of Hepatitus C Virus Using Sera from Patients; The Journal of Immunology, 1996, 156, pp. 4504-4513.
Lenstra, Johannes A., et al.; Isolation of Sequences From a Random-Sequence Expression Library That Mimic Viral Epitopes, Journal of Immunological Methods, 1992, 152, pp. 149-157.
Carlos,Maria P., et al.; Antibodies From HIV-Positive and AIDS Patients Bind to an HIV Envelope Multivalent Vaccine, Journal of Acquired Immune Deficiency Syndromes, 1999, 22, pp. 317-324.
Carlos, Maria P., et al.; Immunogenicity of a Vaccine Preparation Representing the Variable Regions of the HIV Type I Envelope Glycoprotein, Aids Research and Human Retroviruses, 2000, 16.2, pp. 153-161.
Jackson, Peter, et al.; Reactivity of Synthetic Peptides Representing Selected Sections of Hepatitis C Virus Core and Envelope Proteins With a Panel of Hepatitis C Virus-Seropositive Human Plasma, Journal of Medical Virology,1997, 61, pp. 67-79.
Anderson, David E., et. al; Overcoming Original (Antigenic) Sin; Clinical Immunology, vol. 101, No. 2, Nov. pp. 152-157, 2001.
Meyer, Debra, et. al; Induction of Cytotoxic and Helper T. Cell Responses by Modified Simian Immunodeficiency Virus Hypervariable Epitope Constructs; Viral Immunology, vol. 12, No. 2, 1999, pp. 117-129, Mary Ann Leibert, Inc.

*Primary Examiner*—T. D. Wessendorf
(74) *Attorney, Agent, or Firm*—Borden Ladner Gervais LLP

(57) ABSTRACT

A process is disclosed for preparation of a immunogenic peptide mixture in a single synthesis. The peptide mixture collectively represents the in vivo variability seen in immunogenic epitopes from a pathogen. The mixture is termed a hypervariable epitope construct (HEC). Immunization with a HEC evokes broadly reactive immunity against divergent strains of a pathogen upon which the HEC is based.

5 Claims, 16 Drawing Sheets

STEP 1:
Obtain immunogenic epitope sequences
of a pathogen containing immunogenic B cell neutralization, CTL and/or
T-helper epitope and having a variable residue within the epitope

↓

STEP 2:
Calculate frequency of amino acids found at a
variable residue position within an epitope

↓

STEP 3:
Round amino acid frequency to the nearest 25%

↓

STEP 4:
For similar amino acids present at variable residue but having a rounded frequency <25%,
pool frequencies and assign pooled frequency to most frequently occurring amino acid.
Round pooled frequency to nearest 25%

↓

STEP 5:
Select most frequently occurring amino acids at a
variable residue, each having a non-zero rounded frequency,
with the caveat that no more than 4 amino acids are selected

↓

STEP 6:
Synthesize a peptide mixture by including the amino acids
selected in step 5 for each variable residue with the caveat that no
more than 100 different peptides are formed in the mixture

↓

| STEP 7: Purify peptide mixture from step 6 | → | STEP 8: Confirm peptide mixture composition | → | STEP 9: Confirm immunogenicity of peptide mixture |

HIV-1 HEC 1

| position | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| % 1st AA | 100 | 100 | 75 | 100 | 100 | 100 | 50 | 100 | 100 | 100 | 100 | 50 | 50 | 100 | 100 | 50 | 100 | 50 | 100 | 100 | 100 |
| 1st AA added | C | T | D | L | K | N | A | T | N | T | N | S | S | S | S | R | M | M | M | E | K |
| % 2nd AA added | | | 25 | | | | 50 | | | | | 50 | 50 | | | 50 | | 50 | | | |
| 2nd AA | | | N | | | | D | | | | | T | T | | | E | | E | | | |

HIV-1 HEC 2

| position | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| % 1st AA | 100 | 100 | 75 | 100 | 100 | 50 | 50 | 100 | 100 | 100 | 100 | 100 | 75 | 100 | 50 | 100 | 100 | 100 | 100 | 50 | 100 |
| 1st AA added | F | Y | K | L | D | I | V | P | I | D | N | T | S | S | S | Y | R | L | I | N | C |
| % 2nd AA added | | | 25 | | | 50 | 50 | | | | | | 25 | | 50 | | | | | 50 | |
| 2nd AA | | | R | | | H | I | | | | | | D | | N | | | | | S | |

HIV-1 HEC 3

| position | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| % 1st AA | 100 | 75 | 100 | 75 | 100 | 50 | 100 | 100 | 100 | 100 | 75 | 100 | 100 | 100 | 75 | 100 | 100 | 50 | 100 | 100 | 75 |
| 1st AA added | T | S | K | S | W | H | N | G | T | W | R | A | F | Y | S | T | G | D | I | G | D |
| % 2nd AA added | | 25 | | 25 | | 50 | | | | | 25 | | | | 25 | | | 50 | | | 25 |
| 2nd AA | | R | | R | | R | | | | | Q | | | | W | | | G | | | N |

HIV-1 HEC 4

| position | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| % 1st AA | 100 | 100 | 100 | 100 | 100 | 50 | 100 | 100 | 100 | 100 | 75 | 100 | 100 | 100 | 75 | 100 | 100 | 50 | 100 | 100 | 100 |
| 1st AA added | F | N | S | T | T | F | N | S | T | E | E | E | E | G | S | N | N | T | E | G | S |
| % 2nd AA added | | | | | | 25 | | | | | 25 | | | | 25 | | | | | | |
| 2nd AA | | | | | | S | | | | | S | | | | W | | | | | | |
| % 3rd AA added | | | | | | 25 | | | | | | | | | | | | | | | |
| 3rd AA | | | | | | P | | | | | | | | | | | | | | | |

HIV-1 HEC 5

| position | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| % 1st AA | 100 | 100 | 100 | 100 | 100 | 100 | 100 | 100 | 100 | 100 | 100 | 100 | 50 | 100 | 100 | 100 | 100 | 100 | 100 | 100 | 100 |
| 1st AA added | T | R | D | G | G | N | N | N | N | E | S | E | I | F | R | P | G | G | G | G | D |
| % 2nd AA added | | | | | | | | | | | | | 50 | | | | | | | | |
| 2nd AA | | | | | | | | | | | | | T | | | | | | | | |

| MONKEY NO.[a] | ANTIGEN | ANTIBODY TITERS (weeks post immunization)[b] | | | | | | | | | | | | | |
|---|---|---|---|---|---|---|---|---|---|---|---|---|---|---|---|
| | | 2 | 4 | 6 | 8 | 11 | 13 | 16 | 20 | 37 | 40 | 76 | 96 | 104 |
| 25705 | HECs 1-5 | 0 | 100 | 1000 | 1000 | >40000 | >40000 | >5000 | >5000 | 1000 | 1000 | 1000 | 1000 | 1000 |
| | HEC 1 | 0 | 100 | 100 | 500 | >40000 | >40000 | >5000 | >5000 | 1000 | 1000 | 1000 | 1000 | 500 |
| | HEC 2 | 0 | 0 | 0 | 0 | >40000 | >40000 | 1000 | 500 | 100 | 100 | 100 | 100 | 100 |
| | HEC 3 | 100 | 500 | 500 | 1000 | >40000 | >40000 | >5000 | >5000 | 1000 | 1000 | 1000 | 1000 | 1000 |
| | HEC 4 | 0 | 0 | 500 | 500 | >40000 | >40000 | >5000 | >5000 | 1000 | 1000 | 1000 | 1000 | 1000 |
| | HEC 5 | 0 | 0 | 1000 | 1000 | >40000 | >40000 | 1000 | 500 | 100 | 100 | 100 | 100 | 100 |
| 25598 | HECs 1-5 | 0 | 100 | 100 | 100 | >40000 | 20000 | >5000 | >5000 | 5000 | 1000 | 1000 | 1000 | 1000 |
| | HEC 1 | 0 | 0 | 0 | 0 | >40000 | 20000 | >5000 | >5000 | 1000 | 1000 | 1000 | 1000 | 1000 |
| | HEC 2 | 0 | 0 | 0 | 0 | 20000 | 5000 | 1000 | 500 | 500 | 500 | 500 | 500 | 500 |
| | HEC 3 | 0 | 100 | 100 | 100 | >40000 | 10000 | >5000 | 1000 | 1000 | 1000 | 1000 | 1000 | 1000 |
| | HEC 4 | 0 | 0 | 100 | 100 | >40000 | 10000 | >5000 | >5000 | 5000 | 1000 | 1000 | 1000 | 1000 |
| | HEC 5 | 0 | 0 | 0 | 0 | 10000 | 5000 | 5000 | 1000 | 100 | 100 | 100 | 100 | 100 |

FIG. 5

| Viral Isolate | Monkey No. | Weeks Post-Immunization | Neutralizing Antibody Titer Inhibition >80% of RT |
|---|---|---|---|
| HIV-1 89.6 | 25705 | Week 11 | 1:160 |
| | | Week 13 | 1:320 |
| | 25598 | Week 11 | 1:160 |
| | | Week 13 | 1:320 |
| | Positive Control | | 1:2560 |
| HIV-1 IIIB | 25705 | Week 11 | 1:2560 |
| | | Week 13 | 1:1280 |
| | 25598 | Week 11 | 1:640 |
| | | Week 13 | 1:320 |
| | Positive Control | | 1:2560 |
| HIV-1 SF162 | 25705 | Week 11 | 1:20 |
| | | Week 13 | 1:40 |
| | 25598 | Week 11 | 1:40 |
| | | Week 13 | 1:160 |
| | Positive Control | | 1:1280 |
| SIVmac239 | 25705 | Weeks 11 & 13 | none |
| | 25598 | Weeks 11 & 13 | none |
| SRV-1 | 25705 | Weeks 11 & 13 | none |
| | 25598 | Weeks 11 & 13 | none |

HCV HEC 1

| position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| % added | 100 | 100 | 100 | 50 | 100 | 100 | 100 | 100 | 100 | 100 | 100 | 100 | 100 | 100 | 100 | 100 | 50 | 50 | 50 | 100 | 100 | 100 | 100 | 100 |
| AA | A | T | T | Y | V | T | G | G | A | A | A | R | A | T | A | G | L | A | S | L | F | S | P | G |
| % added | | | | 50 | | | | | | | | | | | | | 50 | 50 | 50 | | | | | |
| AA | | | | H | | | | | | | | | | | | | F | T | N | | | | | |

HCV HEC 2

| position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| % added | 100 | 100 | 75 | 100 | 75 | 100 | 75 | 100 | 100 | 100 | 75 | 100 | 100 | 100 | | | | | | | | | | |
| AA | I | S | Y | A | N | G | S | G | P | D | Q | R | P | Y | | | | | | | | | | |
| % added | | | 25 | | 25 | | 25 | | | | 25 | | | | | | | | | | | | | |
| AA | | | H | | D | | G | | | | H | | | | | | | | | | | | | |

| position | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| % 1st AA added | 100 | 50 | 100 | 50 | 50 | 100 | 100 | 100 | 100 | 100 | 100 | 100 | 100 | 100 | 100 | 100 | 100 | 50 | 50 | 100 | 50 |
| 1st AA | E | T | G | K | R | G | G | K | S | S | G | S | S | Y | P | V | L | N | V | S | Y |
| % 2nd AA added | | 50 | | 50 | 50 | | | | | | | | | | | | | 50 | 50 | | 50 |
| 2nd AA | | P | | S | H | | | | | | | | | | | | | S | K | | M |
| Influenza-based HEC 1 | | | | | | | | | | | | | | | | | | | | | |
| % 1st AA added | 50 | 50 | 50 | 100 | 100 | 100 | 50 | 100 | 100 | 100 | 100 | 100 | 100 | 50 | 100 | 100 | 100 | 100 | 50 | 50 | 100 |
| 1st AA | K | K | G | S | V | H | H | P | S | T | I | T | E | Q | T | S | L | Y | V | N | A |
| % 2nd AA added | 50 | 50 | | | | | 50 | | | | | | | | | | | | 50 | 50 | |
| 2nd AA | E | S | | | | | K | | | | | | | | | | | |

FIG. 16

| Construct | Amino acid(s) added at each position during peptide synthesis: |
|---|---|
| gp 120-1 | C T N V N T N T T N T T S S G T M E K G E M K N C |
| 64 variants |   D L   N   T                     E   I   T S |
|  |                                                       S |
| gp 120-2 | M T E L R D K K Q K E Y A L F Y R L D V P I D N N S T |
| 64 variants | I S     I     V V            K |
| gp 120-3 | R K S I R I G P G Q A F Y A T G D I I G D I R Q A H C |
| 32 variants |        H          R T        E |
| gp 120-4 | C N S T Q L F N S T W S T E G S N N T E G S D T |
| 32 variants |   T S       G     T     Y                   N |
| gp 120-5 | G N N N S S N E I F R P G G G |
| 48 variants |   S T N     T T |
|  |   T |

SEQUENCE LISTING

```
<160> NUMBER OF SEQ ID NOS: 16

<210> SEQ ID NO 1
<211> LENGTH: 21
<212> TYPE: PRT
<213> ORGANISM: Human immunodeficiency virus type 1

<400> SEQUENCE: 1

Cys Thr Asp Leu Lys Asn Ala Thr Asn Thr Asn Ser Ser Ser Arg
1               5                   10                  15

Met Met Met Glu Lys
            20

<210> SEQ ID NO 2
<211> LENGTH: 21
<212> TYPE: PRT
<213> ORGANISM: Human immunodeficiency virus type 1

<400> SEQUENCE: 2

Phe Tyr Lys Leu Asp Ile Val Pro Ile Asp Asn Thr Thr Ser Ser Tyr
1               5                   10                  15

Arg Leu Ile Asn Cys
            20

<210> SEQ ID NO 3
<211> LENGTH: 21
<212> TYPE: PRT
<213> ORGANISM: Human immunodeficiency virus type 1

<400> SEQUENCE: 3

Thr Ser Lys Ser Ile His Ile Gly Pro Gly Arg Ala Phe Tyr Thr Thr
1               5                   10                  15

Gly Asp Ile Gly Asp
            20

<210> SEQ ID NO 4
<211> LENGTH: 21
<212> TYPE: PRT
<213> ORGANISM: Human immunodeficiency virus type 1
```

-continued

```
<400> SEQUENCE: 4

Phe Asn Ser Thr Trp Phe Asn Ser Thr Trp Ser Thr Glu Gly Ser Asn
1               5                   10                  15

Asn Thr Glu Gly Ser
            20

<210> SEQ ID NO 5
<211> LENGTH: 20
<212> TYPE: PRT
<213> ORGANISM: Human immunodeficiency virus type 1

<400> SEQUENCE: 5

Thr Arg Asp Gly Gly Asn Asn Asn Asn Glu Thr Glu Ile Phe Arg Pro
1               5                   10                  15

Gly Gly Gly Asp
            20

<210> SEQ ID NO 6
<211> LENGTH: 24
<212> TYPE: PRT
<213> ORGANISM: Hepatitis C virus

<400> SEQUENCE: 6

Ala Thr Thr Tyr Val Thr Gly Gly Ala Ala Ala Arg Ala Thr Ala Gly
1               5                   10                  15

Leu Ala Ser Leu Phe Ser Pro Gly
            20

<210> SEQ ID NO 7
<211> LENGTH: 14
<212> TYPE: PRT
<213> ORGANISM: Hepatitis C virus

<400> SEQUENCE: 7

Ile Ser Tyr Ala Asn Gly Ser Gly Pro Asp Gln Arg Pro Tyr
1               5                   10

<210> SEQ ID NO 8
<211> LENGTH: 21
<212> TYPE: PRT
<213> ORGANISM: Influenza A virus

<400> SEQUENCE: 8

Glu Thr Gly Lys Arg Gly Gly Lys Ser Ser Gly Ser Ser Tyr Pro Val
1               5                   10                  15

Leu Asn Val Ser Tyr
            20

<210> SEQ ID NO 9
<211> LENGTH: 21
<212> TYPE: PRT
<213> ORGANISM: Influenza A virus

<400> SEQUENCE: 9

Lys Lys Gly Ser Val His His Pro Ser Thr Ile Thr Glu Gln Thr Ser
1               5                   10                  15

Leu Tyr Val Asn Ala
            20

<210> SEQ ID NO 10
<211> LENGTH: 21
```

<212> TYPE: PRT
<213> ORGANISM: Influenza A virus

<400> SEQUENCE: 10

Asn Gly Leu Phe Ser Lys Glu Ser Pro Asn Asn Lys Asn Lys Asp Pro
1               5                   10                  15

Ile Asp Thr Cys Asp
            20

<210> SEQ ID NO 11
<211> LENGTH: 21
<212> TYPE: PRT
<213> ORGANISM: Influenza A virus

<400> SEQUENCE: 11

Tyr Val Ser Val Ser Ser Ser Arg Ile Ala Ser Arg Pro Lys Val Arg
1               5                   10                  15

Gly Gln Gly Asp Thr
            20

<210> SEQ ID NO 12
<211> LENGTH: 28
<212> TYPE: PRT
<213> ORGANISM: Human immunodeficiency virus type 1

<400> SEQUENCE: 12

Cys Thr Asn Val Asn Thr Asn Asn Thr Thr Asn Thr Thr Ser Ser Ser
1               5                   10                  15

Gly Gly Thr Met Glu Lys Gly Glu Met Lys Asn Cys
            20                  25

<210> SEQ ID NO 13
<211> LENGTH: 30
<212> TYPE: PRT
<213> ORGANISM: Human immunodeficiency virus type 1

<400> SEQUENCE: 13

Met Thr Thr Glu Leu Arg Asp Lys Lys Gln Lys Glu Tyr Ala Leu Phe
1               5                   10                  15

Tyr Arg Leu Asp Val Val Pro Ile Asp Asn Asn Ser Thr Ser
            20                  25                  30

<210> SEQ ID NO 14
<211> LENGTH: 27
<212> TYPE: PRT
<213> ORGANISM: Human immunodeficiency virus type 1

<400> SEQUENCE: 14

Arg Lys Ser Ile Arg Ile Gly Pro Gly Gln Ala Phe Tyr Ala Thr Gly
1               5                   10                  15

Asp Ile Ile Gly Asp Ile Arg Gln Ala His Cys
            20                  25

<210> SEQ ID NO 15
<211> LENGTH: 24
<212> TYPE: PRT
<213> ORGANISM: Human immunodeficiency virus type 1

<400> SEQUENCE: 15

Cys Asn Ser Thr Gln Leu Phe Asn Ser Thr Trp Ser Thr Glu Gly Ser
1               5                   10                  15

Asn Asn Thr Glu Gly Ser Asp Thr

```
<210> SEQ ID NO 16
<211> LENGTH: 15
<212> TYPE: PRT
<213> ORGANISM: Human immunodeficiency virus type 1

<400> SEQUENCE: 16

Gly Asn Asn Asn Ser Ser Asn Glu Ile Phe Arg Pro Gly Gly Gly
1               5                   10                  15
```

IMMUNOGENIC FORMULATION AND PROCESS FOR PREPARATION THEREOF

RELATED APPLICATIONS

This application is a continuation-in-part of U.S. patent application Ser. No. 09/414,484 filed Oct. 8, 1999, now abondoned which is entitled to the benefit of U.S. provisional patent application Ser. No. 60/103,642, filed Oct. 9, 1998.

FIELD OF THE INVENTION

The present invention relates generally to an immunogenic formulation and a process for its preparation. More particularly, the present invention relates to a process for preparing an immunogenic peptide mixture based on selected amino acids occurring at a variable residue of a protein epitope.

BACKGROUND OF THE INVENTION

Many pathogens, including viruses such as HIV-1 and HIV-2, influenza, hepatitis A/B/C, human papillomavirus (HPV), and dengue, as well as parasites such as malaria and trichinella, can readily alter the amino acid sequence within particular protein epitopes. In view of this behavior and for other purposes, synthetic peptide vaccines are increasingly being explored as alternatives to attenuated or inactivated vaccines. By selection of only those epitopes that confer an effective immunity, epitopes responsible for deleterious immune responses, such as enhancement of disease or T-cell suppression, can be excluded from candidate vaccines. Additionally, as they are chemically defined and lack any infectious material, they pose minimal health risks. Finally, unlike live attenuated vaccines which must be transported and stored at defined, refrigerated temperatures, peptide vaccines are relatively stable and do not require refrigeration, thus making distribution far easier and less costly.

Currently, synthetic peptide vaccines are being evaluated for protection against bacteria, parasites, and viruses. Bacterial epitope vaccines include those directed against Cholera and Shigella. A synthetic vaccine against malaria has undergone phase I and phase II clinical trials in humans. Influenza and hepatitis B viruses represent two viral systems in which synthetic vaccines look especially promising, and there has been much recent interest in synthetic vaccines against human immunodeficiency virus (HIV).

Despite recent advances, synthetic peptide vaccines have been unable to account for envelope or surface protein variability. Several groups have attempted in the past to account for epitope variability using a variety of approaches. One approach to address epitope variability has been described by Tam in U.S. Pat. No. 5,229,490 (Jul. 20, 1993). This process involves conjugating several similar or different epitopes to an immunogenic core by using lysine functional groups and glycine linkers (called dendritic polymers). This process is referred to as a multiple antigen peptide system (MAPS). While highly immunogenic, HIV-based MAPS have not proven to induce broadly reactive antibodies that can recognize divergent strains of virus (Nardelli et al. (1992) J Immunol 148:914–920).

Another early approach involved the identification of 'mimotopes,' which are randomly generated sequences which mimic antigenic epitopes (Lenstra et al. (1992) J Immunol Methods 152:149–157). Using this approach, degenerate oligonucleotides are inserted into bacterial expression vectors, resulting in an expression library of random peptides 6–8 amino acids in length. Those peptides that mimic antigenic epitopes are identified using sera (containing antibodies) from animals or individuals infected with the pathogen of interest. Indeed, this general approach has been used to identify mimotopes that are recognized by sera from HCV-infected individuals (Prezzi et al. (1996) J Immunol 156:4504–4513). However, the peptides are randomly selected and there is a necessity to acquire and analyse sera from infected subjects in order to formulate the mimotope composition.

A further disadvantage to prior art approaches requiring sera from infected individuals is that many infected individuals do not manage to create appropriate anti-pathogen antibodies. Thus, selecting peptides of interest using patient sera could potentially lead to the omission of important antigenic peptides that mimic epitopes against which infected individuals have been unable to mount an immune response.

Using the SIV:rhesus macaque model for HIV infection of humans a, SIV envelope glycoprotein B cell neutralization and T cell epitope has been described and a synthetic immunogen was designed and synthesized based on the hypervariable and highly antigenic epitope of the SIV-mac142 envelope glycoprotein (gp130) (Anderson et al. (1994) Vaccine 12:736–740). This synthetic immunogen consisted of a mixture of peptides representing permutations of amino acid substitutions found in SIV envelope gene sequences. Thus, the synthetic immunogen collectively represented all the in vivo variability observed for this particular epitope. Immunogenicity of this synthetic immunogen was evaluated, and it was shown to induce enhanced amounts of antibodies in immunized rhesus macaques with binding to native biological SIV. Furthermore, it enhanced immunoreactivity to divergent epitope analogs. In this and a subsequent publication (Meyer et al (1998) AIDS Res Human Retro 14:751–760) it was demonstrated that this approach could account for epitope variability.

In recent years it has become clear that T cells are degenerate in their recognition of peptide antigens. This discovery has raised concerns that peptides from some foreign antigens may mimic some self antigens and inadvertently lead to the activation of autoreactive T cells and the onset of autoimmune disease. Consequently, there would be a risk of autoimmune disease associated with immunization of animals or human with a mixture of randomly synthesized peptides. Mimotope processes (Lenstra et al. (1992) J Immunol Methods 152:149–157) select a subset of peptides for immunization from a mixture of randomly synthesized peptides using sera from infected animals or humans, and thus reduces the risk of autoimmune disease. However, the synthetic immunogen formulations described above (Anderson et al. (1994) Vaccine 12:736–740; Meyer et al (1998) AIDS Res Human Retro 14:751–760) do not contain completely random mixtures of peptides, as the peptides generated are based on the addition of only a few of the possible 20 amino acids at only some steps of the synthesis reactions. Nonetheless, synthetic immunogenic formulations such as those described in the prior art may contain over 8,000 different peptide antigens. While this process led to an immunogen which evoked broadly reactive immunity, the formulation was too complex to characterize biochemically or immunologically, and immunization of humans which such a compound would carry with it a significant risk of autoimmune disease. Further, without full compositional analysis, regulatory approval of a mixed peptide composition is not likely to be obtained. Full compositional analysis for a mixed peptide composition having hundreds or thousands of different peptides would be extremely time-consuming, and is unlikely to be cost-effective.

Many of the previously described synthetic immunogenic formulations are mixtures of tens of thousands of different peptides. Given that T cells are degenerate in their recognition of foreign antigens, mixtures of peptides this complex pose the risk of containing peptides which mimic self antigens, which upon immunization could induce a pathogenic autoimmune response. Moreover, the complexity of previous synthesis schemes made it difficult if not impossible to chemically define and assess the quality of multiple individual preparations of the same composition.

On this basis, there is a need for a new process for the design of an immunogenic peptide mixture resulting in a less complex formulation than those described in the prior art, while retaining optimum immunogenicity. Such a new process would allow such mixtures to be prepared and analysed for human use. Further, there is a need for development of assays to be run on such a preparation in order to ensure the integrity and antigenicity of the mixture formed in the synthesis reaction.

SUMMARY OF THE INVENTION

It is an object of the present invention to obviate or mitigate at least one disadvantage of previous immunogenic formulations or previous processes for preparing such formulations.

The invention provides a process by which a mixture of peptides representing the observed in vivo sequence variants of a protein epitope is formed. A peptide mixture so formed evokes broadly reactive immunity and is useful for production of vaccines, therapeutic agents, and diagnostic kits against pathogenic organisms such as viruses and parasites. The process can be applied to a wide range of epitopes in a pathogenic organism.

The invention provides a process for preparing a mixture of peptides, termed a hypervariable epitope construct (HEC), that collectively represents the in vivo variability seen in immunogenic epitopes, yet is simple enough in its composition to allow for analysis. This mixture represents permutations of amino acid substitutions found within an epitope. Upon immunization of a subject with the mixture of peptides, potent T helper cell and B cell responses are induced, which results in high titers of antibodies with enhanced binding to distantly related native pathogen proteins. In addition, these antibodies can neutralize the infectivity of divergent strains of pathogens upon which the HEC is based.

In a first aspect, the present invention provides a process for preparation of an immunogenic peptide mixture comprising the steps of: obtaining immunogenic epitope sequences of a pathogen, the immunogenic epitope sequences having a common residue region and at least one variable residue with which the sequences differ from each other; determining the frequency with which different amino acids are found at a variable residue of the immunogenic epitope sequences; and synthesizing a peptide mixture comprising up to about 100 different peptides, each peptide having the common residue region and having at a variable residue position an amino acid selected from those found at the variable residue of the immunogenic epitope sequences with a frequency greater than a threshold frequency of from about 10% to about 30%.

Additionally, the invention provides a process for preparation of an immunogenic peptide mixture comprising the steps of: obtaining immunogenic epitope sequences of a pathogen, the immunogenic epitope sequences having a common residue region and at least one variable residue with which the sequences differ from each other; determining the frequency with which different amino acids are found at a variable residue of the immunogenic epitope sequences; rounding the frequency with which an amino acid is found at a variable residue to the nearest 25%; and synthesizing a peptide mixture comprising up to about 100 different peptides, each peptide having the common residue region and having at a variable residue position an amino acid selected from those most frequently found at a variable residue of the immunogenic epitope sequences, provided the amino acid has a non-zero rounded frequency; wherein the variable residue position is selected from two to four different amino acids, each of the two to four different amino acids being represented in the peptide mixture in proportion to its rounded frequency.

In a further embodiment, there is provided a peptide mixture immunogenic to a pathogen, the mixture comprising up to about 100 different peptides, each peptide having a common residue region and having a variable residue position; the common residue region of the different peptides being non-variable amino acids of an immunogenic epitope sequence of a pathogen, adjacent a variable residue of the immunogenic epitope sequence; and the variable residue position being occupied by an amino acid selected from the group consisting of the most frequently occurring amino acids at the variable residue of the immunogenic epitope sequence provided that: (a) no more than four different amino acids are present at the variable residue position of the different peptides of the peptide mixture; and (b) an amino acid present at the variable residue position of the different peptides appears at the variable residue of the immunogenic epitope sequence with a frequency greater than a threshold frequency of from about 10% to about 30%.

The invention differs from previous approaches to preparing immunogenic compositions in that it has been modified in order to make the process suitable for the design of vaccines to be used in humans in that the composition is limited to a small number of peptides which are highly representative of the variability found in native immunogenic epitope sequences.

The invention provides a simple process for producing an immunogenic formulation comprised of a mixture of peptides termed a hypervariable epitope construct (HEC). The peptide synthesis portion of the process can be simply conducted as a "one stage" method using chemical synthetic processes known in the art.

Advantageously, the invention provides various HECs based on different viral epitopes that are synthesized using the process of the invention to produces a large pool of peptides with a minimum of synthesis steps. The number of different peptides produced is controlled in such a way that the full composition of the immunogenic formulation can be predicted and verified by analysis. The inventive HEC is capable of generating broad immunological reactivity with proteins from which the peptides are derived.

Advantageously, after immunization with a HEC, the broad immunological reactivity with divergent strains of a pathogen induced leads to enhanced neutralization of pathogen infectivity.

The inventive HEC is capable of overcoming major histocompatibility (MHC) restriction, which is a common barrier to world-wide human vaccine development. Further, a HEC can be modified to induce a cellular (CTL) immune response. In addition to vaccines, HECs can be used as the basis of diagnostic kits.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 2 is a diagrammatic representation of the process for preparation of a peptide mixture according to an embodiment of the invention.

FIG. 3 illustrates the amino acids selected for synthesis of five HECs based on human immunodeficiency virus type 1 (HIV-1) according to the invention.

FIG. 5 illustrates the potent antibody titers induced in monkeys by immunization with the HIV-1 HECs 1 to 5.

FIG. 7 indicates that antibodies obtained from monkeys immunized with the HIV-1 HECs 1 to 5 neutralize infection of human peripheral blood lymphocytes (PBLs) by divergent strains of HIV-1.

FIG. 9 describes the design of two HECs based on hepatitis C virus (HCV).

FIG. 10 describes the design of four HECs based on the antigenic shift combination sites found on the hemagglutinin envelope protein of Influenza A.

FIG. 16 illustrates the composition of five peptide mixtures comprising a number of peptides Seq. ID. Nos. 12–16 as determined according to the invention.

DETAILED DESCRIPTION

Figure 1:
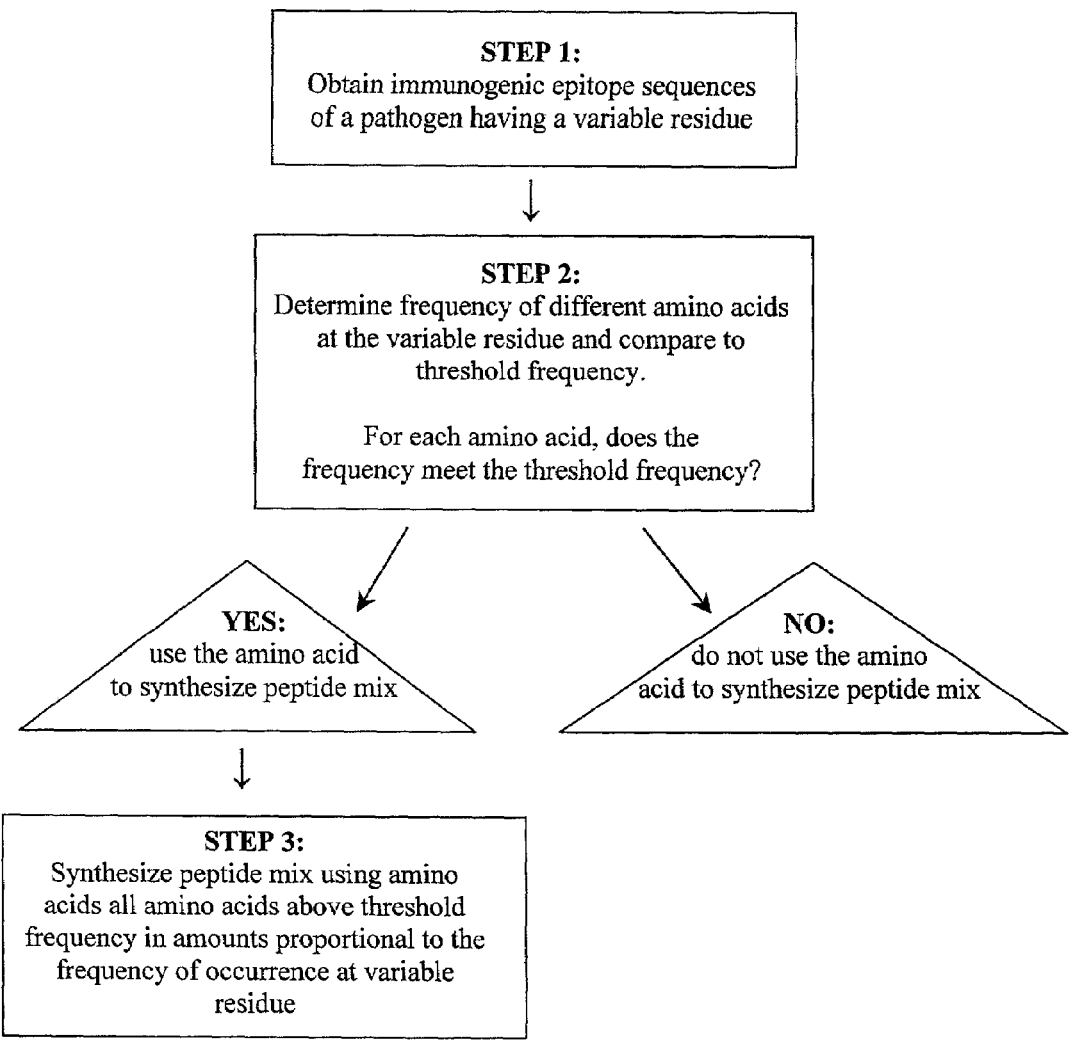
FIG. 1 is a simplified schematic for the synthesis of a HEC according to an embodiment of the invention.

Generally, the present invention provides a process for preparation of an immunogenic peptide mixture, or hypervariable epitope construct (HEC).

In one embodiment, the process for preparation of an immunogenic peptide mixture comprising the following steps. Immunogenic epitope sequences of a pathogen are obtained which have a common residue region and at least one variable residue with which the sequences differ from each other. The frequency with which different amino acids are found at a variable residue of the immunogenic epitope sequences is determined. A peptide mixture is then synthesized which comprises up to about 100 different peptides, each peptide having the common residue region and having, at a variable residue position, an amino acid selected from those found at the variable residue of the immunogenic epitope sequences with a frequency greater than a threshold frequency of from about 10% to about 30%, for example 20%. According to this embodiment, the peptide mixture comprises sequences having at the variable residue an amino acid selected from those most frequently found as the variable residue in the immunogenic epitope sequences, optionally with the restriction that no more than 4 different amino acids appear at the variable residue position of different peptides within the peptide mixture.

During the step of synthesizing the peptide mixture, peptides may be formed so that the different amino acids appearing at the variable residue position are present relative to each other in proportion to the frequency with which each different amino acid appears at the variable residue of the immunogenic epitope sequences. The frequency with which an amino acid is found at a variable residue can be rounded to the nearest 25%, and amino acids could be selected as only those having a non-zero rounded frequency for inclusion at the variable residue position in the peptides of the peptide mixture. In this case, the peptides of the peptide mixture may have a given amino acid present at the variable residue position with a frequency proportional to its rounded frequency.

Optionally, the frequencies of similar amino acids found at a variable residue may be pooled, and the pooled frequency is then assigned to the most frequently found of the similar amino acids when calculating the rounded frequency. As an optional caveat in this case, the frequencies of similar amino acids found at a variable residue can be pooled only if the similar amino acids individually have a frequency below the threshold frequency. The frequencies of similar amino acids may be pooled if, upon rounding each similar amino acid frequency to the nearest 25%, no similar amino acid has a rounded frequency of 25% or greater.

According to the invention "similar" amino acids are selected from those found in a common group, among the groups consisting of: aromatic amino acids; aliphatic amino acids; aliphatic hydroxyl side chain amino acids; basic amino acids; acidic amino acids; amide-containing amino acids, and sulphur-containing amino acids.

According to the invention, the step of synthesis can be conducted using amino acid coupling, wherein the variable residue position is coupled by adding amino acids in proportion to their rounded frequencies. The invention may also include one or more steps conducted using a bioinformatics methodology.

Optionally, the immunogenic epitope sequences comprise from 2 to 7 variable residues, and may result in a peptide mixture contains from 2 to about 64 different peptides.

The invention also relates to process for preparation of an immunogenic peptide mixture comprising a slightly different series of steps, in particular, the following. Immunogenic epitope sequences of a pathogen are obtained which have a common residue region and at least one variable residue with which they differ from each other. The frequency with which different amino acids are found at a variable residue of the immunogenic epitope sequences is determined and rounded to the nearest 25%. A peptide mixture is then synthesized comprising up to about 100 different peptides, each having the common residue region and having, at a variable residue position, an amino acid selected from among those most frequently found at a variable residue of the immunogenic epitope sequences, provided the rounded frequency is non-zero. According to this process the variable residue position is selected from two to four different amino acids, each of which are represented in the peptide mixture in a quantity proportional to its rounded frequency.

This process may comprise the additional steps of pooling the frequencies of similar amino having rounded frequencies less than 25%; assigning the pooled frequency to the most frequently occurring of the similar amino acids; rounding the pooled frequency to the nearest 25%; and, for non-zero rounded frequencies, including the most frequently occurring of the similar amino acids in the step of synthesizing a peptide mixture.

The invention also relates to a peptide mixture immunogenic to a pathogen. The mixture comprises up to about 100 different peptides, each having a common residue region and a variable residue position. The common residue region of the different peptides is formed of non-variable amino acids of an immunogenic epitope sequence of a pathogen, adjacent a variable residue of the immunogenic epitope sequence. The variable residue position is occupied by an amino acid selected from the most frequently occurring amino acids at the variable residue of the immunogenic epitope sequence provided that: (a) no more than four different amino acids are present at the variable residue position of the different peptides of the peptide mixture; and (b) an amino acid present at the variable residue position of the different peptides appears at the variable residue of the immunogenic epitope sequence with a frequency greater than a threshold frequency of from about 10% to about 30%. The frequency with which an amino acid appears at a variable residue position may be determined according to the following scheme: the frequency with which an amino acid occurs at the variable residue of the immunogenic epitope sequence is rounded to the nearest 25%, and amino acids having non-zero rounded frequencies are found at the variable residue position of the different peptides with a frequency proportional to the rounded frequency.

The frequency with which similar amino acids having a rounded frequency less than 25% appear at a variable residue position may be determined by pooling the frequencies of similar amino acids and rounding the pooled value to the nearest 25%. For non-zero rounded frequencies, the rounded frequency is assigned to the most frequently occurring of the similar amino acids. According to this embodiment, the most frequently occurring of the similar amino acids is found at the variable residue position of the different peptides with a frequency proportional to the rounded frequency.

A conjugated peptide composition may be formed according to the invention comprising the inventive peptide mixture conjugated to a lipid moiety, or conjugated to a carrier protein moiety.

The inventive immunogenic composition may comprise a plurality of peptide mixtures formed according to the inventive process, wherein each of the peptide mixtures is immunogenic to the same pathogen. Optionally, immunogenic composition according to the invention, may include a plurality of peptide mixtures directed to different immunogenic epitopes of the same pathogen, and the different immunogenic epitopes may be found in regions in close proximity on the pathogen surface.

A vaccine may be formed according to the invention invoking an immunogenic response against a pathogen. The vaccine comprises the inventive peptide mixture in combination with a pharmaceutically acceptable carrier. Thus a method of vaccination against a pathogenic disease according to the invention comprises the step of administering to a subject an effective amount of this vaccine.

A method of diagnosing infection of a subject by a pathogen falls within the scope of the invention. The method comprising the steps of: obtaining an antibody-containing biological sample from a subject; contacting the biological sample with the immunogenic peptide mixture according to the invention, based on immunogenic epitope sequences of the pathogen; and evaluating immunogenic response of the sample with the peptide mixture. A diagnostic kit for determining infection of a subject by a pathogen may comprise the immunogenic peptide mixture according to the invention, based on immunogenic epitope sequences of the pathogen, along with directions for evaluating an immunogenic response of an antibody-containing biological sample of the subject with the immunogenic peptide mixture.

Further, the invention provides a process for isolating an antibody immunogenic to a pathogen comprising the steps of: administering to a subject the peptide mixture according to the invention; and obtaining from the subject an antibody, or a part of the antibody reactive with the pathogen, said antibody being induced by administration of the peptide mixture.

A process for isolating a gene encoding an antibody immunogenic to a pathogen may be conducted according to a further aspect of the invention. The process comprises the steps of: administering to a subject the peptide mixture according to the invention; obtaining an antibody from the subject induced by administration of the peptide mixture; and isolating a gene encoding the antibody. Similarly, a process for isolating a portion of a gene or genetic material encoding an antibody immunogenic to a pathogen may be conducted according to the invention, comprising the steps of: administering to a subject the peptide mixture according to the invention; obtaining an antibody from the subject induced by administration of the peptide mixture; and isolating the portion of a gene or genetic material encoding the antibody. Thus, an immunotherapy against a pathogen can be developed involving administration of a peptide or protein encoded by a portion of the gene or genetic material obtained according to this process.

The process for preparing the immunogenic mixture according to the invention begins with a comprehensive examination of naturally occurring sequences of a given pathogen that have been reported in scientific databases or peer-reviewed scientific journals. This serves to reduce the number of different peptides produced during synthesis. The amino acid(s) that are added, and at what steps during the peptide synthesis reaction they are added, are determined a priori according to specified process steps, after first aligning sequences that span known T helper cell and B cell neutralization epitopes. The resulting mixture of peptides, termed a hypervariable epitope construct (HEC), represents epitope sequence permutations generated in a single peptide synthesis by adding statistically weighted mixture(s) of amino acid(s) to be linked to prior assembled amino acids on the nascent peptide chain. Thus, unlike mimotopes, the peptides contained in a HEC are not completely random and are already expected to represent an antigenic epitope of interest. For this reason, there is no necessity to use sera from infected animals or patients to isolate the epitopes of interest. HECs can be tested for reactivity against sera from pathogen-infected individuals as an aspect of quality control, to ensure that the peptide synthesis reaction proceeds properly. At no point is patient serum used to select individual peptides contained within a HEC, which is a fundamental difference from the prior art mimotope approach.

The invention represents a simple process that has been developed to account for epitope variability. During solid-phase peptide synthesis, an amino acid is "coupled" or added to resin beads at each cycle to form a growing peptide chain. The percentage of an amino acid added at a particular cycle is calculated according to the invention, based on the frequency with which the amino acid is found at a specific location in an epitope. This information is based on sequence information, derived from data obtained directly in a lab through amino acid sequencing, or is derived from in vivo sequence data obtained from sequence databases, and/or peer-reviewed scientific literature. The inventive immunogenic peptide mixture or HEC, consists of a mixture of peptides representing permutations of amino acid substitutions found within a protein epitope.

A schematic diagram of the process for preparing a HEC is illustrated in FIG. 1. Briefly, in step 1, the sequences of an immunogenic epitope of a pathogen are obtained. The epitope has at least one variable residue represented by different amino acids in the various known sequences. The frequency with which each different amino acids occurs at the variable residue of the epitope sequences is determined in step 2, and compared to a pre-determined threshold frequency. A threshold frequency is set so that amino acids represented in relatively small amounts in the epitope sequences fall below the threshold and thus will not be represented in the resulting peptide mixture. Those amino acids meeting the threshold frequency are candidates for addition during the peptide synthesis in step 3 at the variable residue position. Those amino acids represented in an amount below the threshold frequency are not used at the variable residue position during peptide synthesis. Finally, synthesis of a peptide mixture is undertaken using any synthetic route so that at the variable residue positions, amino acids above the threshold frequency are added in amounts proportional to the frequency with which the occur in the immunogenic epitope. The threshold frequency may range from 10% to 30%, and the resulting synthetic peptide mixture should not be so complex so as to contain more than about 100 different sequences.

An alternative schematic diagram of the process for preparing a HEC is illustrated in FIG. 2. Briefly, in step 1, protein sequences of in vivo isolates of a given pathogen are obtained from appropriate sources such as databases or peer-reviewed journals. The protein sequences are aligned, particularly with reference to those sequences containing immunogenic B cell neutralization, CTL, or helper epitopes, if present. Note that it is not necessary to identify a specific immunogenic B cell neutralization, CTL, or helper epitope in a given protein sequence used in the invention. Although an epitope represents a region of a protein that some aspect of the immune system has chosen to target, it is not necessary to identify the mechanism by which the immune system acts in order for an epitope to be used in the invention.

In step 2, the frequency with which an amino acid appears at each position within an epitope of interest is determined. For those positions having more than one amino acid appearing, the amino acids are included in the peptide mixture according to a particular set of rules defined in steps 3 to 6. In particular, frequencies are rounded to the nearest 25% for each amino acid appearing at the variable residue position (step 3). For example, a frequency of 12% is rounded downward to 0%, whereas a frequency of 13% is rounded upward to 25%.

In step 4, for similar amino acids present at a variable residue but having a rounded frequency less than 25%, the frequencies are pooled, and the pooled frequency is assigned to the most frequently occurring of the similar amino acids. This value is then rounded to the nearest 25%.

Similar amino acids can be considered as those having similar chemical structures or properties which render them conservatively exchangeable. Examples of such similar amino acids are aliphatic amino acids (Gly, Ala, Val, Leu, Ile, and Pro), amino acids containing aliphatic hydroxl side chains (Ser, Thr), sulphur-containing amino acids (Cys, Met), aromatic amino acids (Phe, Tyr, and Trp), basic amino acids (Lys, Arg, and His), acidic amino acids (Asp, Glu), and amide-containing amino acids (Asn, Gln).

As an example of this step, if methionine is present at a frequency of 10% and cysteine is present at a frequency of 8%, neither amino acid alone can be rounded to 25%. However, because methionine and cysteine are similar amino acids (both are sulphur-containing amino acids) their frequencies are added together to make a pooled frequency of 18%, which rounds to 25% and this frequency is then assigned to methionine which occurs more frequently than cysteine at the variable residue.

In step 5, those amino acids found at the variable residue and having a non-zero rounded frequency (for example, a frequency of 25%, 50%, 75% or 100%) are added during the peptide synthesis in amounts proportional to their rounded frequency. If the sum of the rounded frequencies to not add up to 100%, the sum of the rounded frequency is used as a devisor by which each rounded frequency is divided in order to arrive at a proportional percentage to use when adding amino acids at the variable residue. For example, if a first amino acid is present at a variable residue with a frequency of 60%, and a second amino acid is present at a variable residue with a frequency of 30%, no other amino acid or pooled combination of amino acids would round to a non-zero frequency. Thus, the first amino acid rounds down to 50%, and the second amino acid rounds down to 25%. Because the total of the first and second rounded frequencies is 75%, the proportions of each amino acid to be added during synthesis can be calculated by dividing each rounded frequency by the total of 75%. Thus, the first amino acid is added in an amount of 50% divided by 75% (or 66.7%) and the second amino acid is added in an amount of 25% divided by 75% (or 33.3%).

Step 4 also involves a caveat that no more than 4 amino acids are chosen for a variable residue. In the case, for example, where 5 different amino acids occur at a variable residue position with an approximately equal frequency of 20%, each amino acid would have a rounded frequency of 25%. Thus, the total of all non-zero rounded frequencies would be 125%. However, because a maximum of 4 amino acids can be added at this step, the 4 most frequently occurring of the five different amino acids would be selected, and the total non-rounded frequency would be 100%. In this case, each of the 4 most frequently occurring amino acids would be added in an amount of 25% at this variable residue.

In step 6 a peptide mixture is synthesized which includes the amino acids selected in step 5. This step may be conducted using any acceptable method of peptide synthesis that allows selective placement of amino acids at particular residues. Known peptide synthesis methods, such as Fmoc chemistry may be used. This step involves the caveat that no more than 100 different peptides are formed in the mixture. To calculate the number of different peptides which will be present in a mixture, the following equation can be used:

For each variable residue of the peptide, the number of different amino acids which may be present is determined. These numbers are multiplied together to arrive at the number of different possible peptides formed in step 6.

For example, an 11-mer having 3 variable residue positions is to be made. The first of the 3 variable positions has 4 different amino acid choices, whereas the remaining 2 variable positions each have only two different amino acid choices. The total number of different possible peptides formed is calculated as: 4×2×2=16. For non-variable residues (the remaining 8 amino acids of the 11-mer), only one amino acid may be used. Thus no extra variability is introduced by the non-variable amino acids.

As a further example of step 6, a peptide mixture based on a 16-residue epitope is formed having 6 variable residues and 10 non-variable residues. Each of the variable residues has a choice of 2 amino acids. The total number of different peptides formed in step 6 can be calculated as 2×2×2×2×2×2 (or $2^6$)=64.

In step 7, the peptide mixture formed in step 6 is purified according to any acceptable process. For example, lyophilization and dialysis can be conducted and repeated as many times as necessary to ensure purity of the peptides. Gel purification or other methods of peptide separation can be used.

In step 8 involved confirmation of the composition of the peptide mixture. This is a quality control step which may be important when working with a new peptide mixture for which no routine purification has yet been developed. This step may be optional once a full procedure is worked up and perfected for a particular immunogenic peptide mixture. Amino acid analysis can be used to ensure that the expected amino acids of the mixture are contained within an HEC. Further, SDS polyacrylamide gel electrophoresis (PAGE) of a HEC can be used to confirm that a HEC contains peptides within the range of expected molecular weights.

In step 9, the immunogenicity of a peptide mixture is confirmed. Again, this step is beneficial if it is the first time that such an HEC is being formed. However, after the immunogenicity of an HEC is known, it is not required to re-confirm efficacy with each synthesis. In order to test immunogenicity, the purified HEC is mixed with an appropriate pharmaceutical carrier, and an adjuvant approved for human use. This composition can be administered to mice and/or rhesus macaques to confirm immunogenicity, or to identify particularly immunogenic HEC compositions if a variety of different HECs are formed. At this point, it may be desirable to obtain sera from a pathogen-infected subject which could then be tested for reactivity against the HECs to ensure antigenicity.

In general, the concept for the process for HEC formation is based on the principle that there are many different protein found within in vivo isolates of a given pathogen which correspond to immunogenic epitopes (for example, those evoking T helper, CTL, and/or antibody responses). These sequences can be obtained from databases and/or peer-reviewed scientific publications, and aligned. The variable amino acid positions are identified as variable residues, together with the different amino acids that occupy each variable residue position. Of the possible twenty naturally-occurring amino acids which exist, variable positions are usually occupied by only a few different amino acids.

According to one embodiment of the invention, using solid phase peptide synthesis and Fmoc chemistry, the amino acids to be added at a given step within the synthesis reaction are determined according to the following guidelines: 1) a mixture of no more than four amino acids is used at any amino acid coupling step in the synthesis, 2) the amount of each amino acid used at any coupling step is determined based on the frequency of each amino acid appearing in the variable residue position, rounded to the nearest 25%, 3) if two or more amino acids occur at a given position at frequencies less than 25% and are similar in their chemical structures or properties, then frequencies of these amino acids will be added, rounded to the nearest 25%, and only the amino acid occurring most frequently among these amino acids will be added, and 4) mathematical calculations predict that one hundred or fewer variants of a given epitope are contained within said mixture.

At each variable position the incoming amino acid is linked with the prior amino acid on the nascent chain by adding a statistically weighted mixture of amino acids. The proportion was established from examination of the known sequences which occurred in vivo. Therefore, one synthetic procedure yields the entire range of variable epitopes. To verify that the cocktail of peptides in the HEC does represent all the variants, amino acid sequencing can be performed on the peptides en bulk to verify that the appropriate amino acids are present.

In addition to their use in vaccination against disease, HECs based on hypervariable epitopes of a given pathogen may also be used to diagnose the infection of an individual with a pathogen which is not easily detected by routine serology. This might occur for lack of a "universal" antigen which can be recognized by antisera from all infected individual regardless of the strain of the pathogen with which an individual is infected.

The invention can also be used to produce a composition (or vaccine) which when used to immunize a subject, such as a human, a primate, or other animal, induces protective antibodies. Upon identification and isolation of the genes which code for these antibodies, the genes and the gene products can in turn be used as therapeutic agents for the treatment of organisms infected with the pathogens upon which the composition is based.

An HEC may be formed with various immunomodulating agents in order to evoke different effector arms of the immune system, such as CTL responses or mucosal immune responses.

The invention relates to a process for preparing a HEC that represents observed in vivo sequence variants of a protein epitope. According to an embodiment of the invention, protein sequences of in vivo isolates of a given pathogen are obtained from literature and/or databases. The sequences are aligned, particularly in the regions of the proteins which contain immunogenic epitopes. The frequency with which amino acids appear at each position within an epitope of interest is calculated such that only those amino acids occurring with a frequency above a threshold frequency are included in the mixture. The threshold frequency is typically a value of from about 10 to about 30. Regardless of the number of amino acids appearing above the threshold frequency, no more than four amino different acids are used at any amino acid coupling step in the synthesis.

Frequencies of amino acids to be added at a given amino acid coupling step may be rounded or may be used as they are. If rounded, the frequencies may be to the nearest 5%, 10% or 25%, for example, for ease of calculation. If two or more amino acids occur at a given position at frequencies less than 25%, and are similar in their chemical structures or properties, then the frequencies of these amino acids can be pooled and optionally rounded. In such a case, only the amino acid occurring most frequently among those amino acids pooled will be added, and in proportion to the pooled frequency. The resulting peptide mixture can be calculated to have about one hundred or fewer peptide variants.

The synthesis of the mixture can be conducted by performing each amino acid coupling step by including the amino acids in amounts reflecting the frequencies (or rounded frequencies) above the threshold frequency. In this way, the mixture of peptides is produced in a single synthesis pathway. The mixture can be analysed to ensure composition, antigenicity, and immunogenicity. The mixture is capable of generating broadly reactive immunity with proteins from which the peptides are derived and each peptide within the mixture has a sequence corresponding to a permutation of amino acid substitutions for an epitope upon which the mixture is based.

The peptide mixture according to the invention may be formed by internally crosslinking the peptides to one another. Alternatively, the peptides within the mixture may be linked to a support polymer, which could be either a synthetic or naturally occurring polymer material, such as a carrier protein. An exemplary a support polymer is the protein from which the mixture of peptides is derived. Advantageously, crosslinking the peptides or combining the peptide mixture with a support polymer can have the effect of drawing the attention of the immune system to the peptide mixture, thereby increasing the immunogenicity of the peptide mixture. Such an approach is also beneficial in cases where the peptide mixture is not sufficiently immunogenic on its own, as the conjugation or crosslinking may increase immunogenicity to an effective level. Standard methods, as are known in the art, can be used to form the crosslinks or to conjugate the peptides to such a carrier.

A diagnostic kit according to the invention contains an efficacious amount of a HEC capable of immunological reactivity with antibodies from organisms infected with a pathogen from which an HEC is derived. Each peptide within the mixture of peptides has a sequence corresponding to a permutation of amino acid substitutions for an immunogenic epitope common in a protein derived from the pathogen.

An therapeutic immunogenic composition can be prepared according to the invention by preparing an HEC, immunizing an animal, such as a primate, with an HEC, and obtaining antibodies and genes encoding the antibodies induced by immunization with the HEC. Such an immunogenic composition, or the genetic information encoding antibodies arising from immunization can be administered to a subject.

A protein epitope for use with the invention may be one present in a protein derived from human immunodeficiency virus type 1 or 2 (HIV-1/2), Influenza, human papillomavirus (HPV), malaria, dengue virus, or trypanosomiasis. Epitopes derived from other pathogens may also be used.

The HEC or mixture of peptides may be suspended in any pharmaceutically acceptable carrier. For example, a HEC may be suspended in saline solution. Further, the HEC may be mixed with an adjuvant.

The invention relates to a vaccine which may have amounts of two or more HECs based on one or more proteins from a single pathogen containing one or more epitopes from which said mixtures of peptides are derived. The amounts of HECs may be equimolar. The equimolar amounts of said mixtures of peptides are internally crosslinked, or linked to a support polymer.

The frequency of an amino acid to be added at a given position in said mixture of peptides is determined only from the frequency of amino acids at that single position, not by the structure or length of the protein sequences or isolates. For example, if there are 10 sequences of an epitope available which vary considerably in length, the only consideration in determining the frequency of amino acids to be added at a given position in said mixture of peptides is the total number of different amino acids at the given position in the epitope upon which the mixture of peptides is based. Once the sequences have been aligned, regardless of the sequence length of each of the 10 sequences, if at the second position all 10 sequences have a single amino acid, then 100% of that amino acid will be used in synthesis of the mixture of peptides.

When frequencies are rounded to the nearest 25% (or 5%, 10% or other selected value), the convention known to those skilled in the art is that any value exactly half-way between two specified integers will be rounded upward to the next highest integer while any value lower than the half-way value will be rounded downward to the lower integer. For example, an amino acid that appeared at the third position in a protein epitope in 30% of all aligned sequences for that epitope would have a rounded frequency of 25% at that position. If, however, an amino acid is present in 38% of the aligned sequences for that epitope, then it would be present in the mixture of peptides at a frequency of 50% at that position. An amino acid present with a frequency of 12% when rounded to the nearest 25% would round down to 0%, and would thus not be included in the mixture, in the absence of other similar amino acids with which the frequency of 12% may be pooled.

While HECs designed specifically for potential use against HIV-1, HCV, and influenza, are disclosed as examples herein, the invention may also be used for vaccination against diseases caused by any other human or animal pathogen having epitope variation. The invention is particularly beneficial for use against those pathogens which have proven difficult to diagnose and protect against because of considerable epitope variation. These include, but are not limited to, HIV-2, HPV, malaria, dengue, and trypanosomiasis.

The above-described embodiments of the present invention are intended to be examples only. Alterations, modifications and variations may be effected to the particular embodiments by those of skill in the art without departing from the scope of the invention, which is defined solely by the claims appended hereto.

General Methodology

The following methodologies were used as with the invention, and particularly with reference to the Examples provided below.

Peptide Synthesis

The peptide mixtures are synthesized by 9-fluoroenyl-methoxycarbonyl (Fmoc) chemistry utilizing high capacity (0.7 mmol/g) Knorr resin with 1% divinylbenzene crosslinker. The resin is neutralized with two additions of a 50% (v/v) piperidine:N', N'-dimethyl formamide (DMF) solution. Subsequently, the resin is washed with DMF and methanol. The appropriate molar amounts of amino acids, based on frequencies for a given position, are added. Coupling is allowed to occur for two hours at room temperature. The resin is again washed with DMF and methanol. Following confirmation of coupling, the resin is washed with DMF and deprotected with 50% piperidine: DMF for 9 minutes. After the last amino acid is coupled, the resin is washed with DMF and methanol. The peptide mixtures are cleaved and deprotected by the addition of a 90% trifluoroacetic acid (TFA), 5% 1,2-ethanedithiol (EDT), 5% water solution to the resin. The resin is incubated at room temperature for 6–12 hours. Resin is then washed with TFA and methanol. The TFA washes containing the peptide are collected.

Peptide mixtures are extracted with cold ether. The peptide/TFA solutions are reduced to a small volume (approx. 1 ml) by evaporation under nitrogen gas. Ether (25 volumes) is added to the peptide solution and mixed. Following incubation for 5 minutes on dry ice, the sample is centrifuged at 1000×g for 5 minutes, and the ether is removed. This extraction process is repeated three times. Subsequently, the peptide mixture solution is extracted three times with ethyl acetate:ether (v/v) (1.5:1) in an identical manner to that of the ether extraction. Following a final ether extraction, the residual ether is evaporated under nitrogen gas, and the peptide mixture is resuspended in water and lyophilized.

Conjugation of HECs to Carrier Proteins.

Following synthesis, some HECs may be conjugated to carrier proteins to enhance their immunogenicity. If so, a ratio of 100 moles HEC:1 mole carrier protein (peptides:carrier) is used. Both the protein and HECs are dissolved in 0.5 M N-methyl-imidazole, pH 6.0, at a concentration of 1 mg/ml. The protein and HEC solutions are combined and 50 moles of 1-ethyl-3-(dimethylaminopropyl) carbodiimide (EDC)/mole of HEC/protein solution is added. The mixture is stirred for 30 minutes at 20° C., and then dialyzed (10 kDa cutoff) extensively in a 5% acetic acid buffer. Following dialysis in double distilled water, the vaccine is lyophilized and stored under vacuum at 20° C.

Immunization of Animals

Mice were obtained from Jackson Laboratories (Bar Harbor, Me.). Mice were immunized with 100 μg of single sequence peptide (SSP) or HEC when conjugated to KLH, or with 200 μg when immunized with carrier-free peptides. The immunogen was dissolved in sterile PBS for use. Primary immunizations were administered subcutaneously at the base of the tail while secondary immunizations were similarly administered subcutaneously at the base of the tail two weeks later.

Rhesus macaques were immunized with the HECs or with HEC/carrier protein complexes a total of 2 times. For each immunization, each monkey received 500 μg of the HECs or HEC/carrier protein dissolved in 250 μl PBS and 250 μl Montanide ISA-51. After extensive vortexing, the emulsion was injected intramuscularly at the deltoid muscle. The boost occurred eight weeks after the initial immunization.

ELISA Assays

Testing for responses to a given HEC was performed by the solid phase enzyme linked immunosorbent assay (ELISA) using standard methodology. Briefly, HECs, peptides, or proteins were dissolved in 0.05 M sodium bicarbonate buffer, pH 9.5, and applied to flat-bottom microtiter plates (Corning, N.Y.). Virus was plated at 500 ng/well while peptides and proteins were plated at 1 μg/well. Following incubation with the test serum, antigen-bound primary antibodies were detected with alkaline phosphatase labeled secondary antibodies (anti-mouse or anti-monkey) (Fisher, Pittsburgh, Pa.). Optical density was measured at 405 nm using an automatic plate reader (BioRad 3550).

Neutralization of Viral Infectivity

Viral stocks were grown in CEM×174 cells obtained from the American Type Culture Collection (ATCC, Rockville, Md.). HIV-1 isolates were obtained from the NIH, NIAID Repository. Cells from this line were used to determine virus titers and also to indicate viral infectivity in the neutralization assay. Serum samples were serially diluted (1:20 to 1:2560) and added in triplicate to a 96-well plate. As positive controls, heat-inactivated sera of an HIV-1 neutralizing antibody obtained from the NIH Repository was used. Negative controls included sera of naive monkeys as well as preimmunization sera of all the test animals. Virus was added at 50 TCID50 (50% tissue culture infective dose) and the plates were incubated for 1 hour. After the incubation, CEM×174 cells were added to control wells (cells alone) as well as to the virus/antibody wells at a concentration of $1\times10^5$ cells/well. Plates were incubated at 37° C. in a $CO_2$ incubator and checked daily for syncytium formation. The neutralizing capabilities of the sera were assessed by testing the reverse transcriptase (RT) activity of a portion of the supernatant on day 8 and the cells were exposed to XTT, a 2,3-bis[2-Methoxy-4-nitro-5-sulfophenyl]-2H-tetrazolium-5-carboxanilide (Sigma, St. Louis, Mo.) to determine viability on day 10. The preimmune sera caused no reduction in RT activity. The highest serum dilution achieving more than 50% reduction in RT activity was determined to be a strong neutralization antibody titer. A 30–50% reduction in RT activity obtained with the highest serum dilution was considered a weak neutralization titer.

T Cell Proliferative Response

The antigens and mitogen (PHA-P, Sigma Chemical Co., St. Louis, Mo.) were plated at a concentration of 1 to 10 μg/well in triplicate into 96 well round bottom plates. Whole blood was obtained from immunized monkeys, diluted 1:2 in PBS, overlayed onto Ficoll gradient (LSM, Organon Teknika Corp., Durham, N.C.) and centrifuged at 200×g for 30 minutes at room temperature. Lymphocytes were collected, washed, counted and adjusted to a concentration of $1\times10^6$ viable cells/ml in RPMI-1640 media containing 10% FCS, L-glutamine and antibiotics. A 0.1 ml lymphocyte suspension was dispensed into each antigen containing well of the 96 well plate(s). The plates were incubated at 37° C. and 5% $CO_2$. Following incubation with mitogen for 3 days or antigen for 6 days, 1 μCi of $^3$H-thymidine for 16–18 hours and immediately harvested onto glass fiber filter paper with a Wallac™ cell harvester. After the addition of aqueous scintillation fluid (Scintisafe, Fisher Scientific), $^3$H-thymidine incorporation was determined by measuring radioactivity in an LKB Wallac 1209 Rackbeta™ liquid scintillation counter. The results were expressed as mean stimulation index (SI) and calculated as mean counts per minute (CPM) of experimental (antigen or mitogen) over the mean cpm of the control (cells alone). A mean SI value higher than 2 was considered significant.

CTL Assay

Splenocytes are suspended in RPMI 1640 tissue culture medium. For specific restimulation, $3\times10^7$ responder cells are cocultured with $1.5\times10^6$ syngeneic, antigen-pulsed splenocytes (irradiated with 20,000 rad) for 5 days in 10 ml of medium in upright 25-ml tissue culture flasks in a humidified atmosphere of $CO_2$ at 37° C. For nonspecific restimulation, the responder cells are cultured overnight in media containing interleukin-2 (IL-2) at 10 IU/ml. Antigen specifically and nonspecifically stimulated splenocytes are harvested after 5 days of culture and washed twice with medium; these serve as effector cells. Specific cytolytic activity of effectors is tested using dilutions of effector cells with $2\times10^3$ $^{51}$Cr-labled target cells (syngeneic splenocytes pulsed for 4 hours with antigen) in 200 µl of medium in 96 round-bottomed wells. A volume of 1001 µl of supernatant is collected and read in a gamma counter. Specific lysis is calculated as follows:

$$\frac{(\text{experimental release} - \text{spontaneous release})}{(\text{total release} - \text{spontaneous release})} \times 100$$

Spontaneous release is represented by the value obtained from target cells without any added effector cells, while total release is determined after lysing labeled target cells with a detergent solution.

EXAMPLES

Example 1

HECs Based on HIV-1

Epitope protein sequences were obtained from the Human Retroviruses and AIDS database (Los Alamos, 1998). Based on the sequence data, five regions of the HIV-1 envelope glycoprotein (gp120) are recognizable as hypervariable areas. These five hypervariable regions include antibody neutralizing, CTL, and/or T helper cell epitopes (HIV Molecular Immunology Database, 1998).

The possible amino acids for each position along a neutralization epitope were determined from sequence information of in vivo isolates of HIV-1 clade B strains and the sequence information for each epitope was aligned and evaluated. Subsequently, some amino acid coupling steps in the synthesis of the neutralizing epitope were performed with a mixture of appropriate amino acids as determined from the observed sequence data. This process was repeated at each amino acid coupling step in the synthesis. Thus, in a single synthesis, a mixture of peptides representing all the observed in vivo variants of the neutralization epitope was produced.

FIG. 3 illustrates an exemplary collection of HECs produced according to the invention, showing the amino acid additions used in the constant and variable residues for the synthesis of five HIV-1 HECs. The HECs are based on the variability observed in epitopic sequences of the hypervariable regions of the envelope glycoprotein (gp120) of HIV-1. This collection of HECs synthesized for use in a human vaccine against HIV-1 in the subject invention is comprised of five different HIV-1 HECs. Each of the five HECs comprises a mixture of less than 100 different peptides. For each of the five epitopes, the gp120 sequences of HIV-1 Clade B strains were aligned to assess both the pattern and nature of the variability. The most commonly observed amino acids at each position along the hypervariable region of interest were selected for addition during the peptide synthesis in accordance with guidelines that are an integral element of the subject invention. More specifically, the amount of amino acid(s) added at a given addition in the synthesis using Fmoc chemistry were rounded to the nearest 25%, and no more than four amino acids were ever added at a given amino acid coupling step. In addition, the calculated number of peptides produced in a HEC synthesis never exceeded 100 different peptides. For example, 64, 32, 64, 6, and 4 distinct peptides are calculated to be present in each of the five HIV-1 HECs, respectively.

FIG. 3 indicates that a said mixture of peptides referred to as "HIV-1 HEC 1" contains a mixture of two amino acids at amino acid positions 3, 7, 12, 13, 16, and 18 with single amino acids at all other positions. Binomial multiplication indicates that a total of 64 variants will be contained within this mixture of peptides. This is derived by a multiplication by a factor of 1 at every position containing a single amino acid and multiplication by a factor of 2 at each of the 6 variable residue positions. The length of the epitope is limited so that no more than 100 different peptides are formed. Thus, for example, the HIV-1 HEC 1 could not extend further if any additional amino acid positions contained more than one amino acid, as 64 variants multiplied by any factor greater than one would result in a mixture of peptides containing more than one hundred variants.

Figure 4:
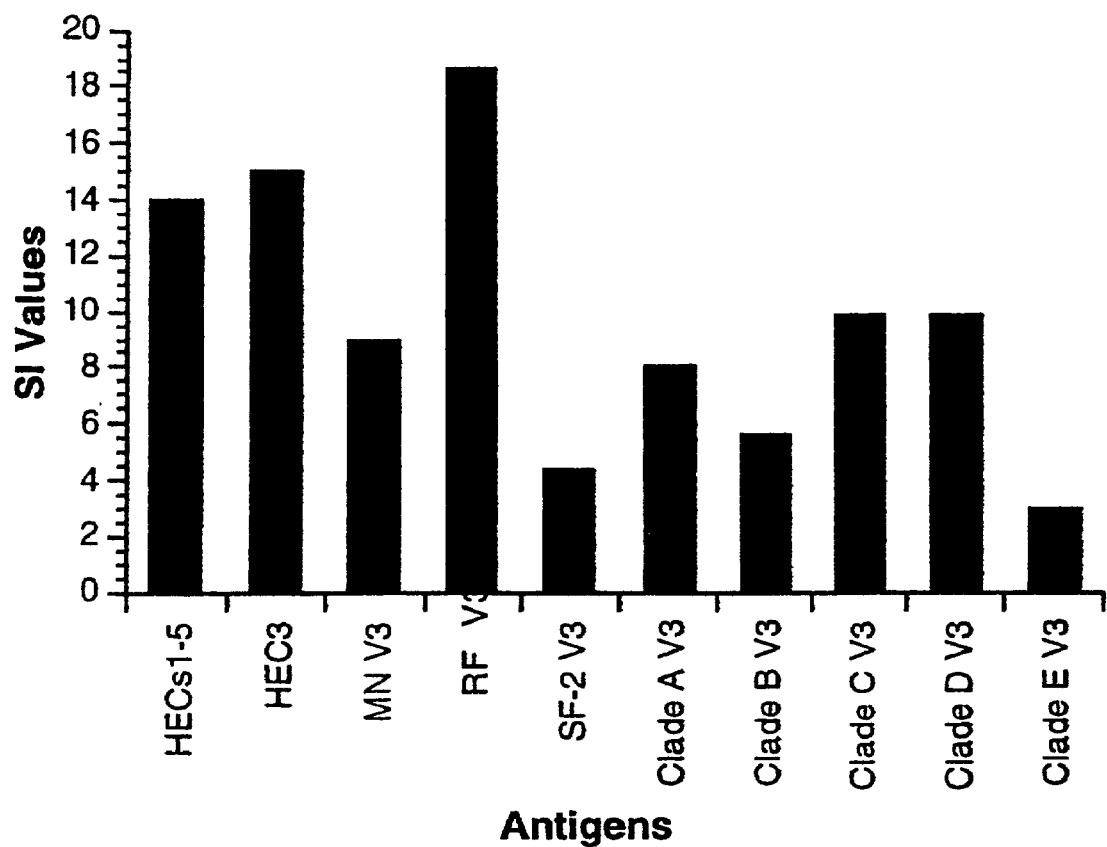
FIG. 4 demonstrates that immunization of non-human primates (monkeys) with the HIV-1 HECs induces T helper cell responses.

To test the immunogenicity of the HIV-1 HECs in primates, two rhesus macaques (Macaca mulatta) were immunized with the HECs, mixed with an adjuvant approved for human use. Peripheral blood lymphocytes (PBLs) were obtained 76 weeks after the previous immunization of the animals with the five HIV-1 HECs. When stimulated in vitro with the HECs as well as with peptides which represent epitopes from divergent strains of HIV-1, the PBLs proliferated extensively, as illustrated in FIG. 4. FIG. 4 also demonstrates that immunization of primates with the HIV-1 HECs results in the induction of T cells that proliferate in response to the highly variable V3 loop sequences from five major, divergent subtypes of HIV-1 (Clades A–E). These data indicate that strong, long-lasting, and broadly reactive T helper cell memory responses can be induced in primates after immunization with these HIV-1 HECs.

FIG. 5 indicates that immunization with the HIV-1 HECs resulted in a long-lasting antibody response directed against the five HECs collectively, and also against the five individual HECs. The induction of broadly reactive T cell help directed against gp120 epitopes from different strains of HIV-1 correlated with broadly reactive antibody binding to divergent epitopes of HIV-1. The monkeys produced antibodies against HIV-1 HEC1, HEC3, HEC4 and HEC5 after the first immunization, and against all the HECs after a second immunization. Thus, immunization with all the HECs at once did not prevent immune responses to be elicited to each of the HECs. The HIV-1 HEC 3 induced a response within two weeks after the first immunization and constituted the strongest antibody response among all five constructs. The antibody titer increased to greater than 1:40,000 after the boost, and remained high, though with a slow decline, for 22 months. The post-immunization health assessment of the monkeys was excellent and the blood chemistry was always normal. No secondary or behavioural symptoms were detected. Sera (containing antibodies) from the immunized monkeys were tested for the presence of broadly reactive antibodies using epitopes found in the gp120 hypervariable regions (V1–V5) of Clade B HIV-1 strains MN, RF and SF2.

Figure 6A:
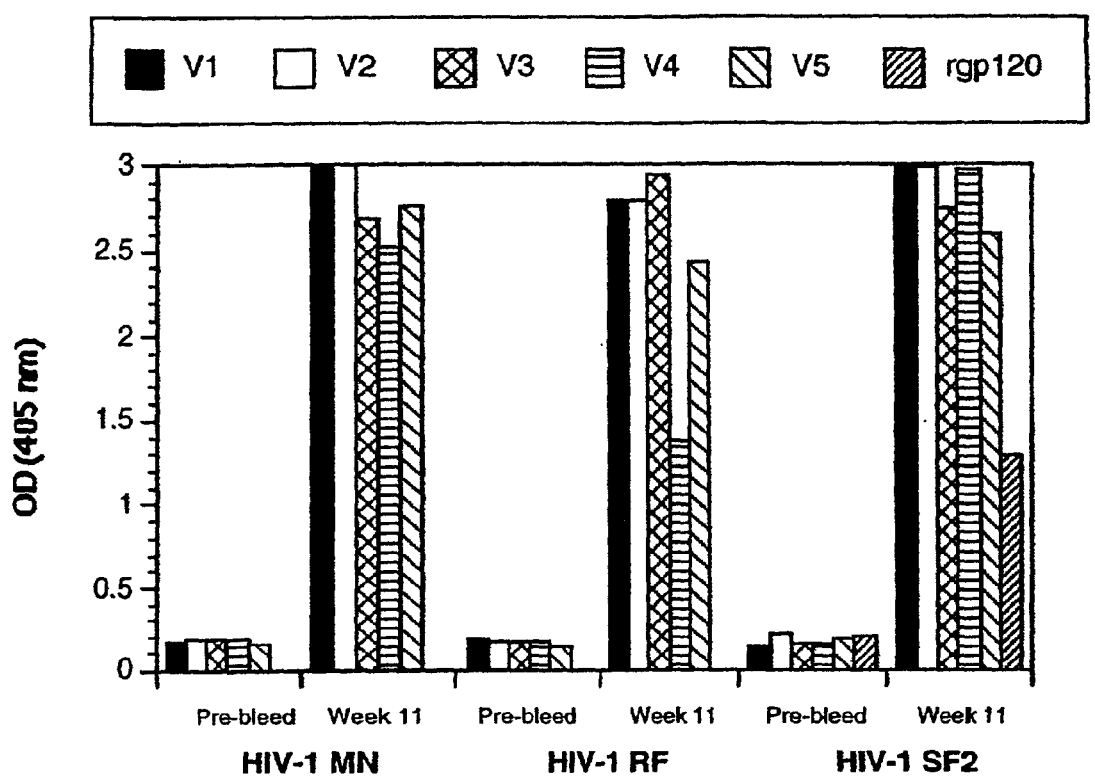
FIG. 6 demonstrates that antibodies induced by immunization with HIV-1 HECs bind to epitopes from divergent strains of HIV-1.
Figure 6B:
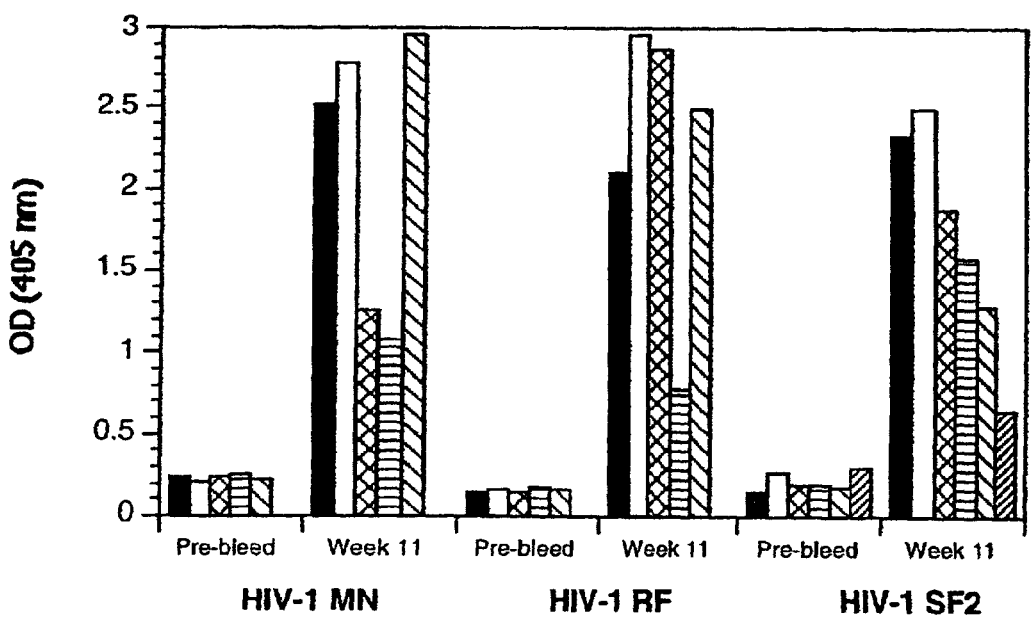

FIG. 6 indicates that two weeks after a second immunization with the HIV-1 HECs, antibody reactivity was observed against all the analogs. Sera from both monkeys (25705 and 25598) bound strongly to all the peptide analogs from all three HIV-1 isolates. More importantly, antibodies from both monkeys were able to recognize and bind to purified HIV-1 SF2 recombinant gp120 protein.

Figure 8:
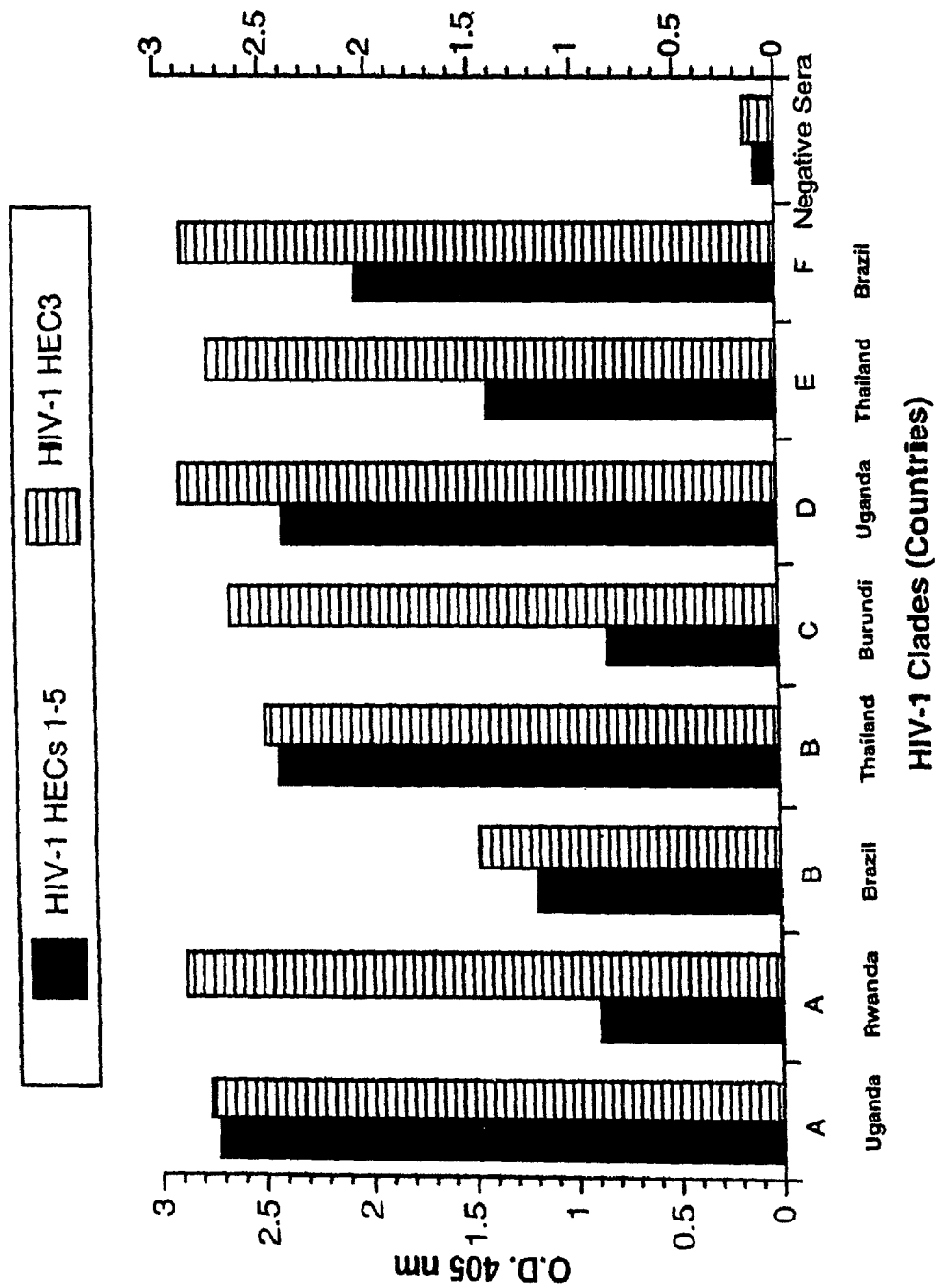
FIG. 8 demonstrates that antibodies from seropositive patients infected with divergent HIV-1 subtypes A, B, C, D, E, and F recognize the HIV-1-based HECs 1 to 5.

FIG. 7 shows that antibodies from the immunized monkeys were tested for neutralizing activity against different HIV-1 laboratory strains and primary isolates. Antibodies from both monkeys were able to neutralize the primary HIV-1 isolate 89.6 and the HIV-1 IIIB laboratory adapted strain of HIV-1. A known neutralizing antibody serum was used as a positive control. The data indicate that immunization of primates with the HIV-1 HECs induces T helper and antibody responses which are broadly reactive against divergent strains of HIV-1. FIG. 8 indicates that, in addition, individuals infected with diverse strains (clades) of HIV-1 from around the world possess antibodies that recognize the HIV-1 HECs.

FIGS. 4–6 of the specification demonstrate that the mixtures of peptides based on HIV-1 envelope protein are immunogenic. FIG. 8 demonstrates their antigenicity, and FIG. 7 illustrates their protective effect against viral replication in vitro.

Example 2

HECs Based on Hepatitis C Virus Epitopes

Two HECs against the two hypervariable regions of hepatitis C virus (HCV) were designed according to the invention. Sequences from in vivo isolates of the viruses were obtained from databases and peer-reviewed scientific literature and the epitopes of interest were aligned. The proportions of amino acids added at individual amino acid coupling steps were then determined according to the guidelines established by the subject invention by rounding amino acid frequencies to the nearest 25% when determining the amino acids to include at a variable residue. FIG. 9 illustrates the amino acids appearing at different positions within the peptide mixture. The peptide mixture was synthesized using standard Fmoc chemistry.

In particular, it can be seen in HCV HEC-1 of FIG. 9 that a 24-mer was formed having equal amounts of tyrosine (Y) and histidine (H) at residue 4, equal amounts of leucine (L) and phenylalanine (F) at position 17, equal amounts of alanine (A) and (T) at position 18, and equal amounts of serine (S) and asparagine (N) at position 19. The number of different peptides generated is thus calculated as 2×2×2×2 (or $2^4$)=16.

Example 3

HECs Based on Influenza Virus Epitopes

Many years of research on influenza have yielded important information that makes the design of HECs based on variation among influenza viruses possible. This data comes from the routine procedures that organizations such as the WHO and CDC have put in place to identify the variants expected to appear during the next year. Briefly, wild isolates of influenza are obtained from various hosts around the world. After they are identified by type (A or B), they are screened against ferret anti-influenza antisera to identify strains that are cross-reactive, and therefore will be protected against by the current influenza vaccine. They are then further screened against a panel of ferret antisera to confirm that the pattern of reactivity is the same. This assures that point mutations have not occurred. In each year, the vast majority of flu strains are antigenically identical. There are always a few strains, however, that produce unique reactivity patterns, and these are carefully studied, since they may become predominant strains in the future. Amino acid sequencing is performed on these unique influenza strains.

FIG. 10 describes four influenza HECs formed according to the invention that collectively represent the antigenic shift combination sites found on the hemagglutinin envelope protein of Influenza A. These HECs differ somewhat from those previously described and characterized in that they represent hypervariable epitopes formed by discontinuous epitopes on the influenza envelope protein. The amino acids chosen in the design of each of these influenza HECs are not from a single, sequential hypervariable stretch of amino acids on the viral surface protein; rather, each is based on amino acids from various portions within the linear amino acid sequence of the viral protein which are thought to exist in close proximity to one another when viewed in three dimensions. The percentages of the amino acids used in synthesis were derived from amino acids of each position based on approximately 61 human isolates of Influenza A (including 5 swine Influenza A sequences) obtained from Genebank and the Swiss Protein database.

Figure 11:
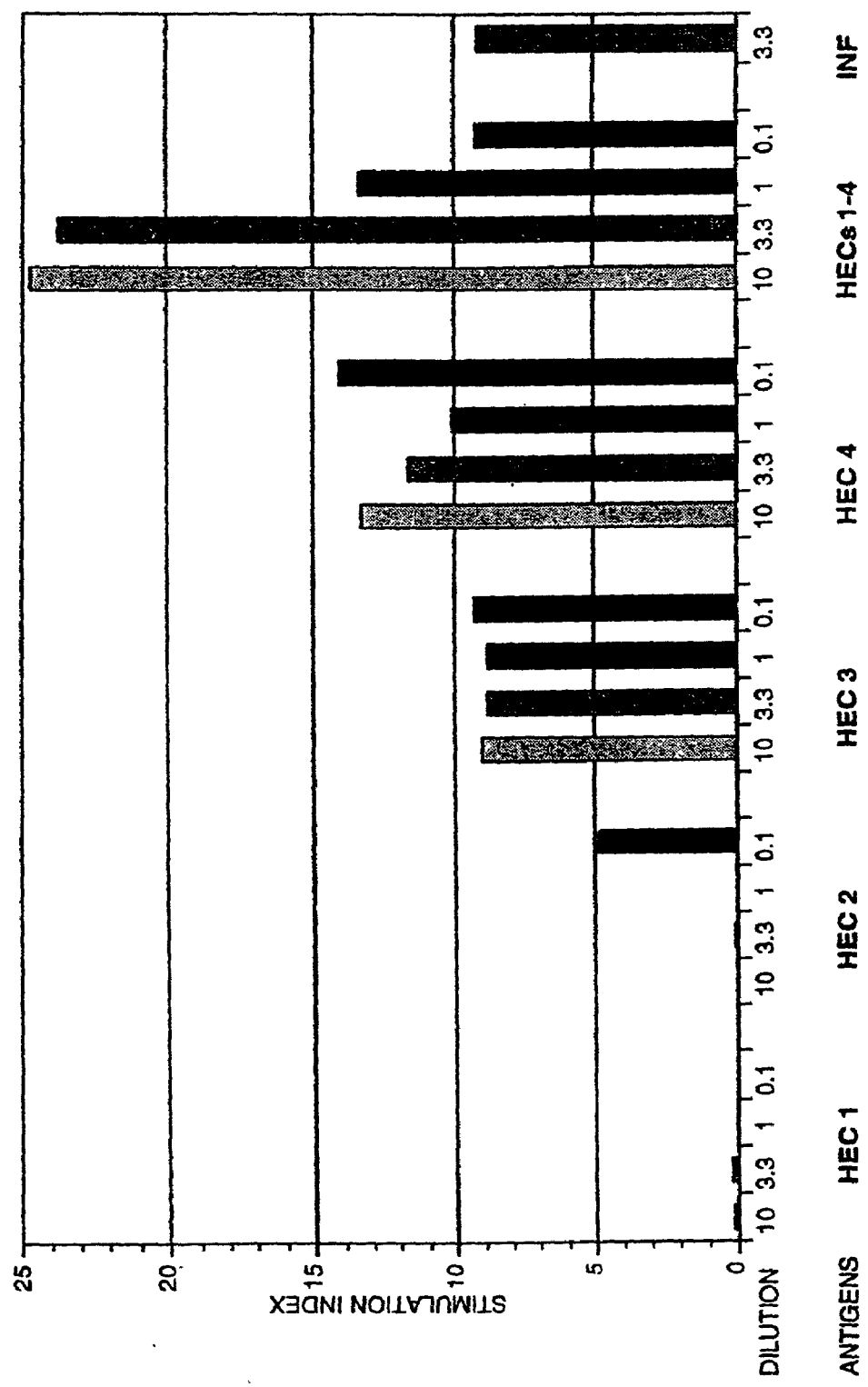
FIG. 11 demonstrates the T helper cell response of mice immunized with the influenza HECs of FIG. 10.
Figure 12:
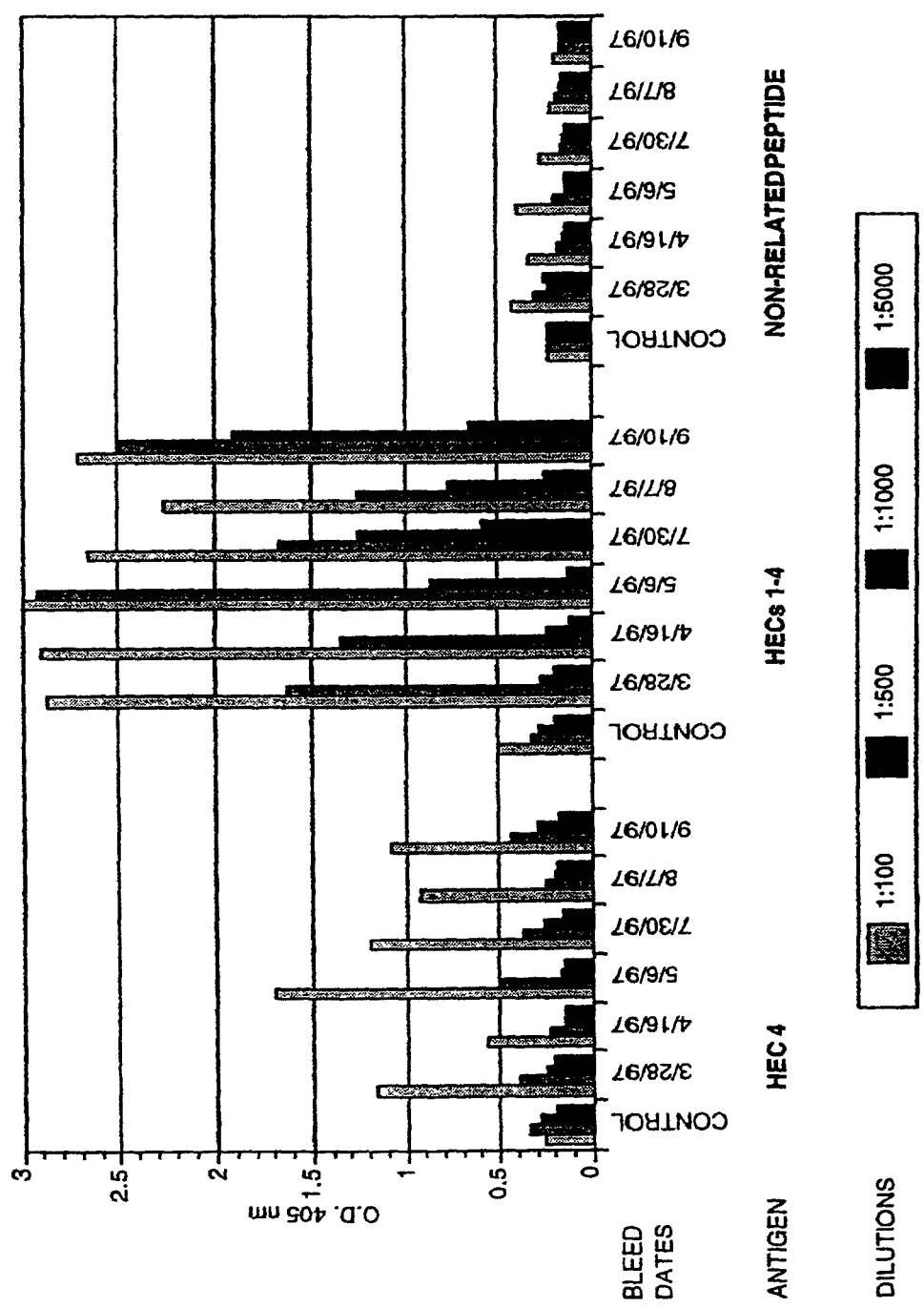
FIG. 12 illustrates the antibody response of mice immunized with the influenza HECs of FIG. 10 as compared with a non-related peptide.

Consistent with results obtained after immunization of monkeys with the HIV-1 HECs, immunization of mice with the four influenza HECs elicited potent T helper cell and antibody responses (FIGS. 11 and 12, respectively). More importantly, T helper cells elicited by immunization with the HECs responded when stimulated in vitro with whole, inactivated, Influenza A virus (FIG. 11).

Figure 13:
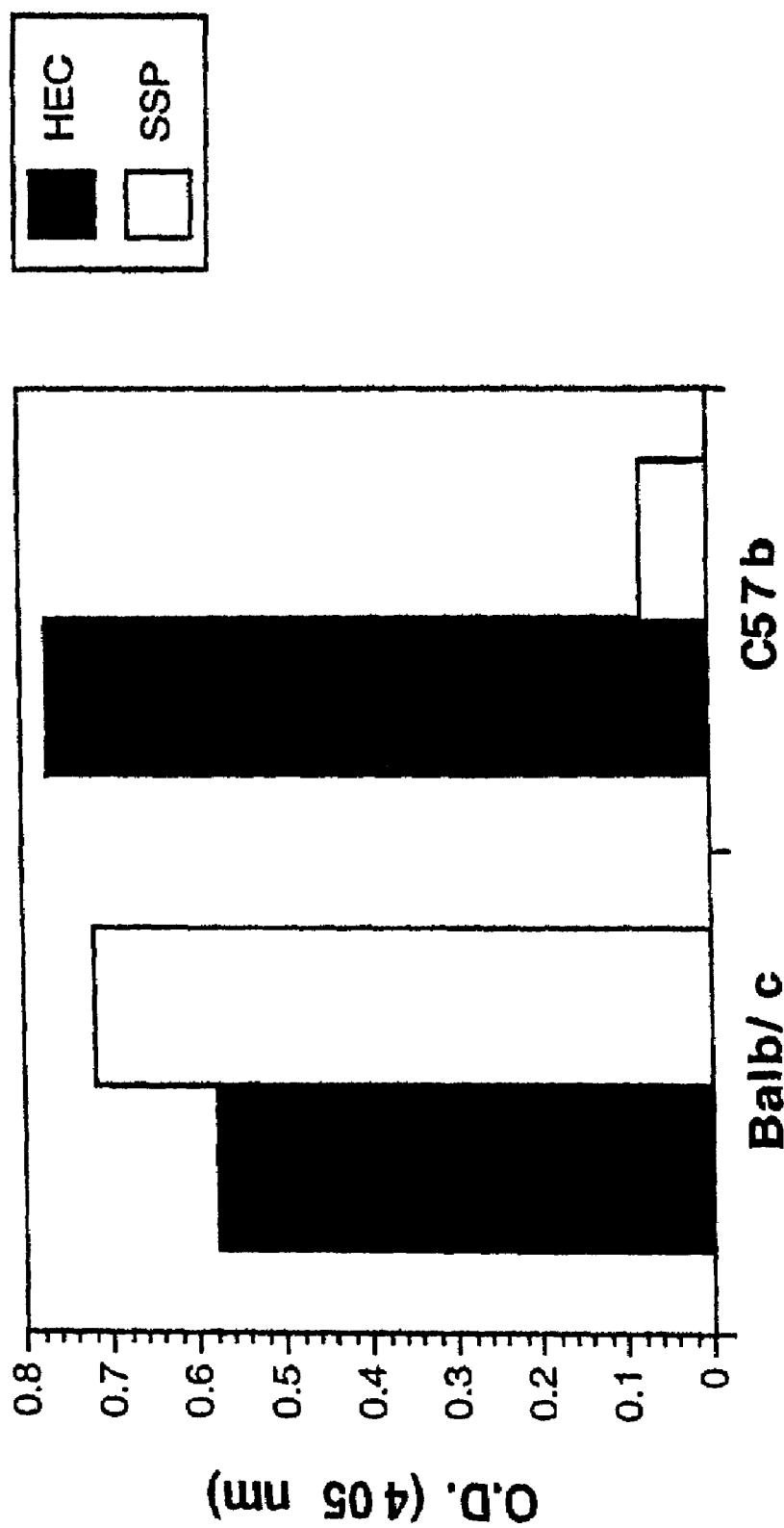
FIG. 13 illustrates the immune response of Balb/c mice after immunization with an SIV-derived HEC. This figure demonstrates that in Balb/c mice, which are unable to evoke an immune response against a single SIV-derived epitope because of their major histocompatibility (MHC) genotype, immunization with a HEC based on this same epitope results in an immune response.
Figure 14:
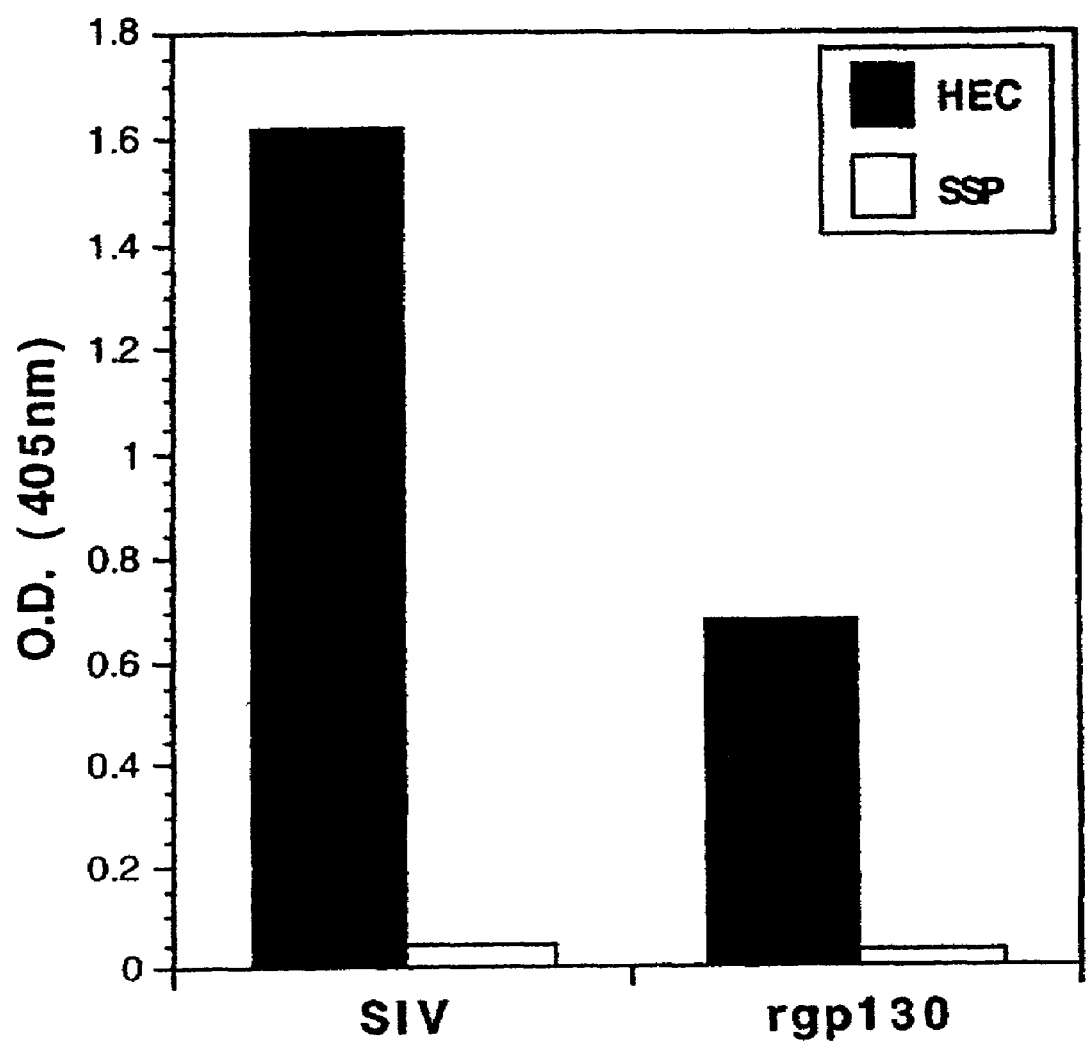
FIG. 14 demonstrates binding of antibodies from mice with SIV. The data demonstrate that the antibodies evoked by immunization of a non-responder strain of mice with the SIV HEC are capable of binding to the virus on which the HEC is based.

A HEC, representing many slightly different variations of an epitope, can help to ensure that in an outbred population in which MHC molecules are highly polymorphic, a HEC is formed which contains a subset of epitope variants capable of binding the groove any individual subject's MHC molecule for presentation to the immune system. Thus, HEC-based vaccines overcome MHC restriction. Indeed, FIGS. 13 and 14 demonstrate this principle. FIG. 13 demonstrates that while immunization of inbred Balb/c mice with a single sequence peptide (SSP) representing the simian immunodeficiency virus (SIV) epitope 414–434 leads to the induction of antibodies which bind this peptide. In contrast, immunization of a genetically different strain of mice (C57bl) with a different MHC restriction cannot produce antibodies that bind to the peptide. However, immunization of the non-responding mice (C57bl), as well as the responding Balb/c mice, with a HEC based on this epitope leads to the induction of antibodies which can bind to the virus as well as the virus protein which contains this epitope (FIG. 14).

Example 4

Conjugation of SIV-Derived HEC with Lipid Moiety

Figure 15:
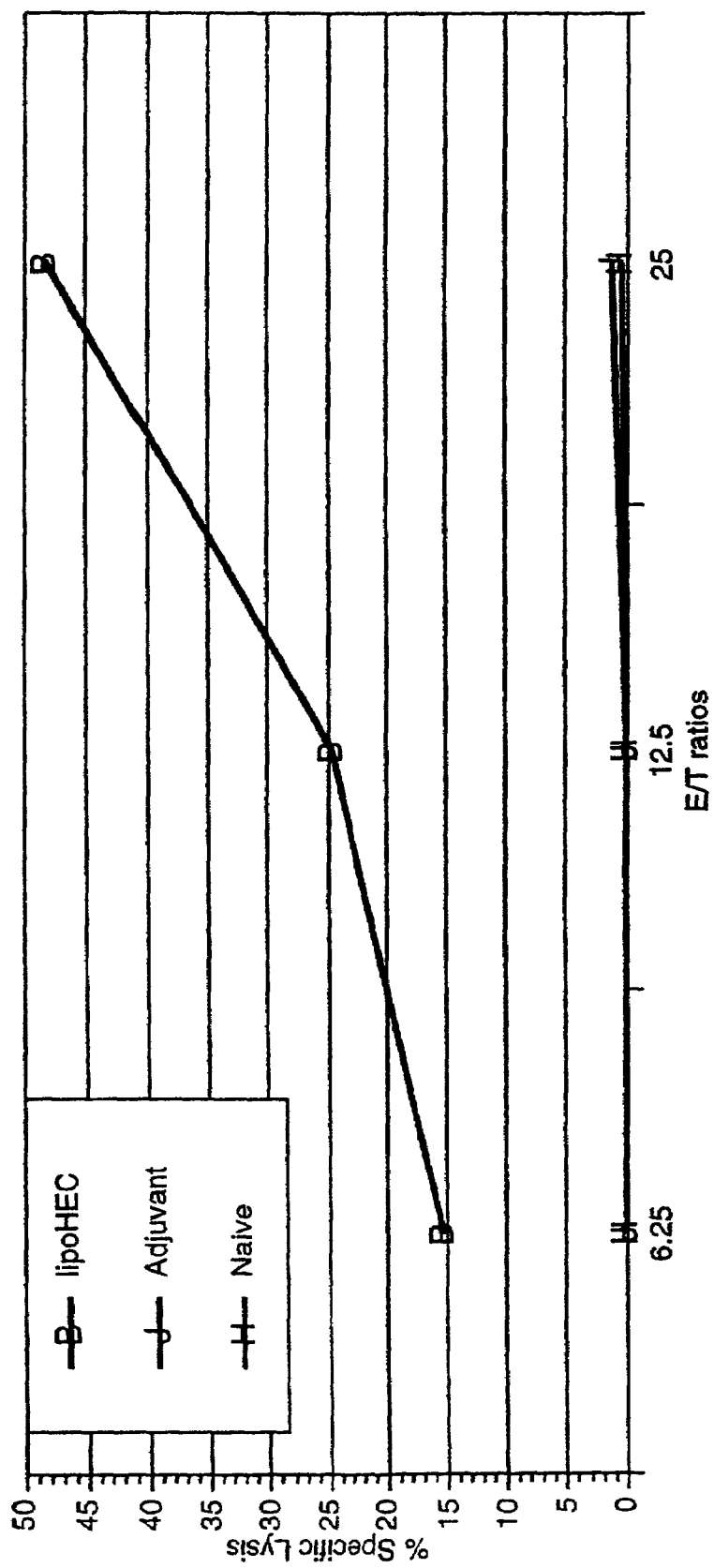
FIG. 15 shows that conjugation of HECs to lipid moieties allows the induction of cytotoxic T lymphocyte (CTL) responses.

In addition to inducing potent T helper cell and antibody responses, HECs can also induce cytotoxic T lymphocyte (CTL) responses when conjugated to lipid moieties. The lipo-HECs used for the induction of CTLs were prepared by conjugating Pam to resin-conjugated HECs based on SIV. This is a standard method for producing lipo-peptides. Mice were immunized with lipo-HEC and adjuvant (lipo-HEC) or with PBS and adjuvant (A-PBS), and splenocytes from these mice as well as from naive mice were tested for CTL activity against target cells incubated with the HECs. Data shown in FIG. 15 depict the percent of specific lysis after subtraction of non-specific background lysis. The observed specific lysis was obtained with animals that received only two immunizations. No lysis was observed after only a single immunization (data not shown). FIG. 15 demonstrates that immunization with lipo-HECs induces significant CTL activity.

Lipo-HECs were also be prepared using a conjugation method in which an ester of palmitic acid is attached to resin-free peptides. The two types of lipo-HEC conjugates were equally effective at inducing immune responses, leading to the conclusion that the conjugation methods do not appear to influence the immunogenicity of the lipo-HECs formed.

Example 5

Formation of Compositions Based on HIV-1 Envelope Glycoprotein

FIG. 16 illustrates sequences for 5 peptide mixtures (or compositions) formed according to the invention. The sequences are based on 5 hypervariable regions of the HIV-1 envelope glycoprotein (gp120). More specifically, the mixtures correspond to epitopes encompassed by the following amino acid sequences in the reference HIV-1 strain B.US.SF2: gp120-1, amino acids 130–155; gp120-2 amino acids 159–193; gp120-3 amino acids 307–333; gp120-4 amino acids 387–410; and gp120-5 amino acids 456–471. At variable residues, where two or more amino acids appear with a frequency of 25% or more when rounded to the nearest 25%, the two or more amino acids are added to the amino acid synthesizing process in quantities representative of their rounded frequencies.

The peptide mixtures formed according to the invention comprise a plurality of different peptides, which reflect the most common variable amino acids found in the HIV-1 envelope glycoprotein (gp120), as reported in the literature. Specifically, gp120-1 to gp120-5 are separate peptide mixtures which contain 64, 64, 32, 32 and 48 different peptides, respectively.

The above-described embodiments of the present invention are intended to be examples only. Alterations, modifications and variations may be effected to the particular embodiments by those of skill in the art without departing from the scope of the invention, which is defined solely by the claims appended hereto.

The invention claimed is:

1. A process for preparation of an immunogenic peptide mixture comprising the steps of:

Obtaining from a database hypervariable immunogenic epitope sequences of a pathogen HCV or influenza virus, said immunogenic epitope sequences having a common residue region and at least one variable residue with which said sequences differ from each other;

determining the frequency with which different amino acids are found at the at least one variable residue of the immunogenic epitope sequences; the at least one variable residue comprising an amino acid selected from the amino acids most frequently found at the variable residue in the immunogenic epitope sequences of the pathogen, and found at the variable residue with a frequency greater than a threshold frequency of about 12%;

rounding the frequency with which an amino acid is found at a variable residue to the nearest 25%, wherein only those amino acids having a non-zero rounded frequency are included at the variable residue position in the peptides of the peptide mixture with the caveat that no more than four amino acids are selected for a variable residue; the frequencies of similar amino acids found individually at a variable residue below the threshold frequency being pooled to form a pooled frequency, the pooled frequency being assigned to the most frequently found of the similar amino acids to calculate the rounded frequency; and synthesizing a peptide mixture comprising from 2 to about 64 different peptides, each peptide having the common residue region and having at a variable residue position an amino acid selected from those found at a variable residue of the immunogenic epitope sequences at a non-zero rounded frequency; the different amino acids appearing at the variable residue position being present relative to each other in proportion to the rounded frequency with which each different amino acid appears at the variable residue of the immunogenic epitope sequences.

2. The process of claim 1 wherein similar amino acids are amino acids belonging to a single classification selected from the group consisting of: aromatic amino acids; aliphatic amino acids; aliphatic hydroxyl side chain amino acids; basic amino acids; acidic amino acids; amide-containing amino acids, and sulphur-containing amino acids.

3. The process of claim 1 wherein the step of synthesizing is conducted using amino acid coupling, and the variable residue position is coupled by adding amino acids in proportion to the rounded frequencies determined in the step of rounding.

4. The process according to claim 1 wherein the pathogen is HCV.

5. The process according to claim 1 wherein the pathogen is influenza.

* * * * *